(12) United States Patent
Ogura et al.

(10) Patent No.: US 6,642,234 B1
(45) Date of Patent: Nov. 4, 2003

(54) ACRYLONITRILE COMPOUNDS

(75) Inventors: Tomoyuki Ogura, Funabashi (JP); Akira Numata, Funabashi (JP); Hideki Ueno, Funabashi (JP); Yoshihide Masuzawa, Funabashi (JP); Toshiro Miyake, Minamisaitama-gun (JP); Yoichi Inoue, Minamisaitama-gun (JP); Norihiko Mimori, Minamisaitama-gun (JP); Shinji Takii, Minamisaitama-gun (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 09/868,061

(22) PCT Filed: Dec. 24, 1999

(86) PCT No.: PCT/JP99/07260

§ 371 (c)(1),
(2), (4) Date: Jun. 14, 2001

(87) PCT Pub. No.: WO00/39106

PCT Pub. Date: Jul. 6, 2000

(30) Foreign Application Priority Data

Dec. 25, 1998 (JP) .......................... 10-369645
Feb. 16, 1999 (JP) ............................ 11-37272
Nov. 30, 1999 (JP) .......................... 11-339519

(51) Int. Cl.⁷ ................. C07D 249/04; C07D 401/06; C07D 403/06; A01N 43/647; A01N 43/78
(52) U.S. Cl. ................ 514/236.2; 546/210; 546/275.4; 514/326; 514/406; 514/365; 514/341; 548/255; 548/204; 544/140
(58) Field of Search .............................. 546/210, 275.4; 514/326, 406, 365, 341, 236.2; 548/255, 204; 544/140

(56) References Cited

U.S. PATENT DOCUMENTS

| | | | |
|---|---|---|---|
| 3,337,565 A | 8/1967 | Bencze et al. ........... | 260/294.9 |
| 3,337,566 A | 8/1967 | Walker et al. ........... | 260/294.9 |
| 4,600,712 A | 7/1986 | Haken et al. ............... | 514/188 |
| 4,639,447 A | 1/1987 | Roeser et al. ............... | 514/222 |
| 4,988,818 A | 1/1991 | Lauer et al. ............. | 548/267.4 |
| 5,064,844 A | 11/1991 | O'Mahony et al. ......... | 514/359 |

FOREIGN PATENT DOCUMENTS

| | | |
|---|---|---|
| DE | 283 916 A | 10/1990 |
| DE | 283 916 A5 | 10/1990 |
| EP | 0 102 163 A1 | 3/1984 |
| EP | 0 412 849 A2 | 2/1991 |
| EP | 0 706 758 A1 | 4/1996 |
| JP | A 52-105167 | 9/1977 |
| JP | A 53-92769 | 8/1978 |
| JP | A 57-502215 | 12/1982 |
| JP | A 59-219228 | 12/1984 |
| JP | A 60-11401 | 1/1985 |
| JP | A 60-11452 | 1/1985 |
| JP | A 60-209571 | 10/1985 |
| JP | A 8-104878 | 4/1996 |
| JP | A 8-145802 | 6/1996 |
| JP | A 8-159346 | 6/1996 |
| JP | A 9-28916 | 2/1997 |
| JP | A 11-124306 | 5/1999 |
| JP | A 11-269173 | 10/1999 |
| WO | WO 95/29591 | 11/1995 |
| WO | WO 97/40009 | * 10/1997 |
| WO | WO 97 40009 A | 10/1997 |
| WO | WO 97/40009 A1 | 10/1997 |
| WO | WO 98 42683 A | 10/1998 |
| WO | WO 98/42683 | 10/1998 |
| WO | WO 99/02507 | 1/1999 |

OTHER PUBLICATIONS

Eiden et al., "Polycarbonylmethyl–Derivate: Reaktionen von 2–(3–Methyl–5–isoxazolyl)–phenylethanon", *Institut fur Pharmazie und Lebensmittelchemie der Universitat Munchen*, pp. 242–251, (1985). (w/abstract).

Eicher et al., "Zur Reakiton von Triafulvenen mit Isonitrilen, Eine einfache Synthese von diphenylsubstituierten funktionalisierten Cyclobuten–Derivaten und deren Folgeprodukten", *Universitat des Saarlandes*, pp. 619–626, (1987). (w/abstract).

(List continued on next page.)

*Primary Examiner*—Mukund J. Shah
*Assistant Examiner*—Hong Liu
(74) *Attorney, Agent, or Firm*—Oliff & Berridge, PLC

(57) ABSTRACT

The present invention relates to acrylonitrile compounds of formula (1):

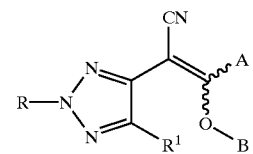

[wherein, R is a $C_1$–$C_6$ alkyl, a $C_3$–$C_7$ cycloalkyl optionally substituted by a $C_1$–$C_4$ alkyl, a naphthyl, etc., $R^1$ is H, a halogen, a $C_1$–$C_6$ alkyl, etc., A is specific 5-membered aromatic heterocyclic ring containing two hetero atoms selected from N, O and S, etc., B is H, a $C_1$–$C_4$ alkyl, a $C_2$–$C_4$ alkoxyalkyl, etc.]

Said compounds are useful as agricultural chemicals, in particular insecticides and acaricides.

12 Claims, No Drawings

OTHER PUBLICATIONS

Ukr, Khim Zh. (Russ. Ed.), 51(6), (1985), pp. 649–652. (w/abstract).

Aberola et al., Produccion Y Transformacion De Carbaniones Derivados De 3,5–Dimetilisoxazoles Funcionalizados En C–4, *Universidad de Valladolid*, vol. 83, pp. 182–194, (1986). (w/abstract).

V. Kantlehner et al., "Umsetzung von 2,5–Dimethyl–1,3,4–thiadiazol mit Saurechloriden", *Chemiker–Zeitung*, vol. 113, pp. 125–127, (1989). (w/abstract).

V. Kantlehner et al., "Umsetzung von 2,5–Dimethyl–1,3,4–thiadiazol mit Carbonsauresstern", *Chemiker–Zeitung*, vol. 113, pp. 217–219, (1989). (w/abstract).

Zirngibl et al., Structure–Activity Relationships of 2–(1H–Imidazol–1yl) vinyl Ethers (Route to the New Broad–Spectrum Antifungal Agent Omoconazole); *Annals New York Academy of Sciences*, pp. 64–73.

Khim–Farm. Zh., 22(10), (1988), pp. 1223–1225. (w/abstract).

Chemical Abstracts, vol. 109, Abstract No. 93171 & Zh. Obshch. Khim., 57(10), (1987), pp. 2234–2249.

Chemical Abstracts, vol. 101, Abstract No. 211021 & Bull. Chem. Soc. Jpn., 57(8), (1984), pp. 2329–2330.

Chemical Abstracts, vol. 96, Abstract No. 217794 & Indian J. Chem., Sect. B, 21B(1), pp. 1–3.

* cited by examiner

ACRYLONITRILE COMPOUNDS

TECHNICAL FIELD

The present invention relates to novel acrylonitrile compounds and agricultural chemicals containing said compounds as an active ingredient. The agricultural chemicals as referred to herein include insecticides, acaricides, nematocides, herbicides and fungicides, etc., and are especially insecticides, acaricides and nematocides in the field of agriculture, horticulture, stock farming and sanitation.

BACKGROUND ART

For acrylonitrile derivatives, WO97/40009 discloses the use thereof as agricultural chemicals.

With the long-term use of insecticides and fungicides, recently, some pests have become resistant to chemicals and are often difficult to exterminate with conventional insecticides and fungicides. Accordingly, it is an object of the present invention to provide novel insecticides and fungicides exhibiting excellent pesticidal activities.

DISCLOSURE OF THE INVENTION

In order to solve the above-mentioned problems, the present inventors have studied to develop compounds described below that exhibit excellent pesticidal activities, in particular exhibit the activities for extremely long term. Consequently, the inventors have completed the present invention.

Specifically, the present invention relates to compounds described in the following [1] to [11] (hereinafter referred to as compounds of the present invention) and agricultural chemicals containing said compounds as an active ingredient described in the following [12].

[11] Acrylonitrile compounds of formula (1):

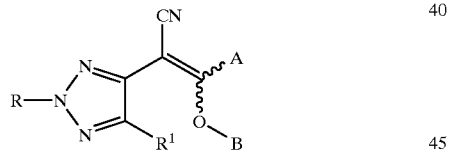

[wherein, R is a $C_1$–$C_6$ alkyl, a $C_3$–$C_7$ cycloalkyl optionally substituted by a $C_1$–$C_4$ alkyl, a phenyl optionally substituted by X, a naphthyl or a pyridyl, $R^1$ is H, a halogen, a $C_1$–$C_6$ alkyl, a $C_3$–$C_7$ cycloalkyl optionally substituted by a $C_1$–$C_4$ alkyl, a $C_1$–$C_6$ alkoxy, a $C_1$–$C_4$ haloalkyl, a $C_2$–$C_6$ alkoxyalkyl, $CH_3OC_2H_4OCH_2$, a $C_2$–$C_6$ alkylsulfenylalkyl, a $C_2$–$C_6$ alkylsulfinylalkyl, a $C_2$–$C_6$ alkylsulfonylalkyl, a $C_1$–$C_3$ alkyl substituted by phenyl, a phenyl, $C_7$–$C_{10}$ phenoxyalkyl, COORa, CONHRb, CONRaRb, CORa, CO(piperidyl), CN, $NO_2$ or $CH_2J$, A is

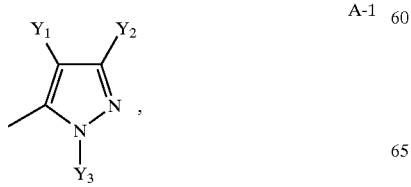
A-1

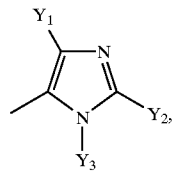
A-2

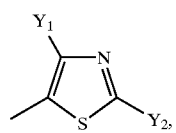
A-3

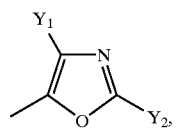
A-4

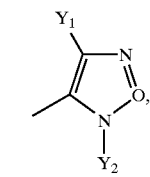
A-5

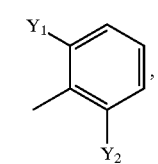
A-6

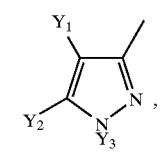
A-7

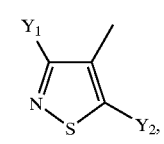
A-8

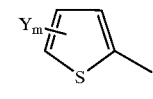
A-9

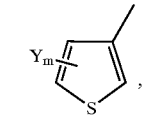
A-10

A-11

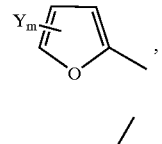
A-12

-continued
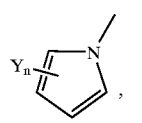, A-13
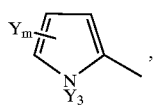, A-14
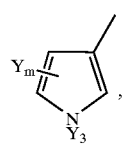, A-15
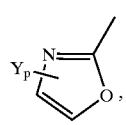, A-16
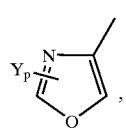, A-17
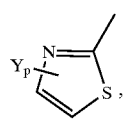, A-18
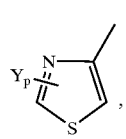, A-19
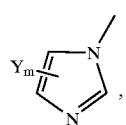, A-20
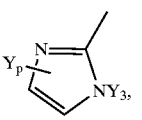, A-21
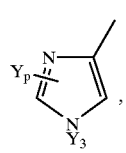, A-22
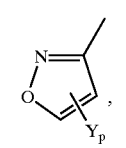, A-23
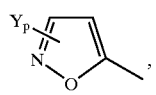, A-24
-continued
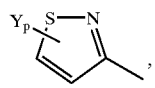, A-25
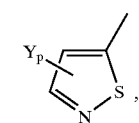, A-26
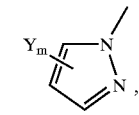, A-27
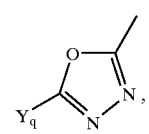, A-28
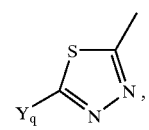, A-29
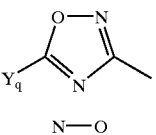, A-30
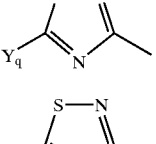, A-31
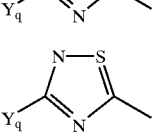, A-32
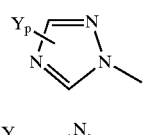, A-33
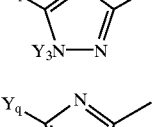, A-34
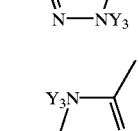, A-35
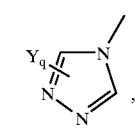, A-36

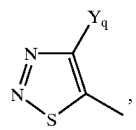
A-39
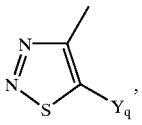
A-40
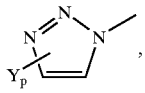
A-41
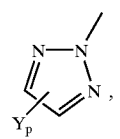
A-42
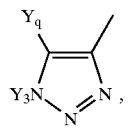
A-43
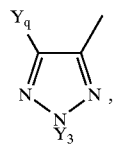
A-44
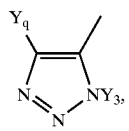
A-45
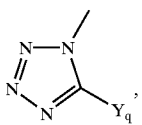
A-46
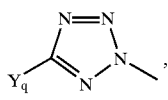
A-47
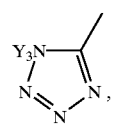
A-48
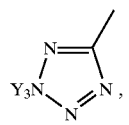
A-49
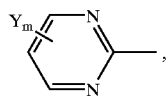
A-50
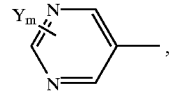
A-51
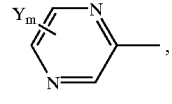
A-52
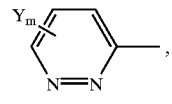
A-53
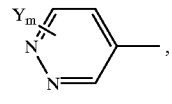
A-54
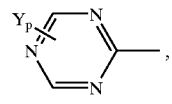
A-55
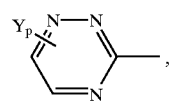
A-56
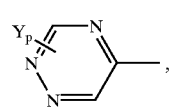
A-57
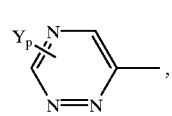
A-58
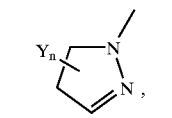
A-59
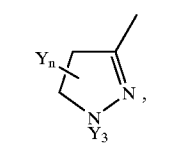
A-60
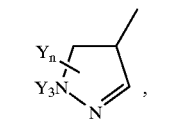
A-61
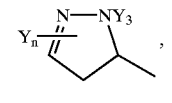
A-62
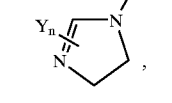
A-63
A-64

-continued
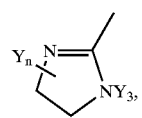 A-65
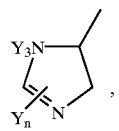 A-66
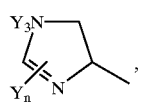 A-67
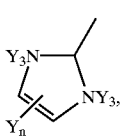 A-68
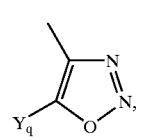 A-69
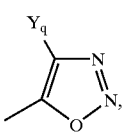 A-70
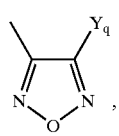 A-71
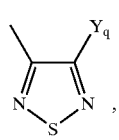 A-72
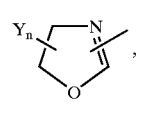 A-73
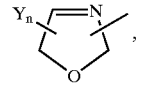 A-74
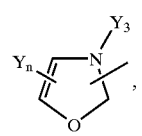 A-75
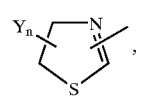 A-76
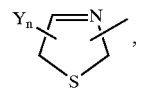 A-77
-continued
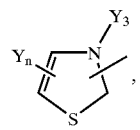 A-78
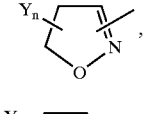 A-79
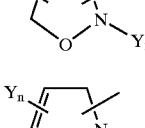 A-80
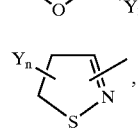 A-81
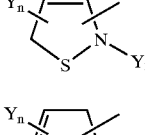 A-82
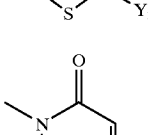 A-83
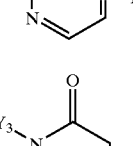 A-84
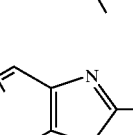 A-85
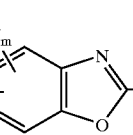 A-86
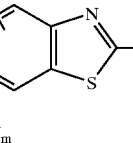 A-87
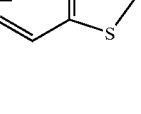 A-88
 A-89
A-90

-continued

A-91 through A-111: chemical structure diagrams of benzofused heterocycles with substituents $Y_n$, $Y_m$, $Y_p$, $Y_q$, and $Y_3$.

-continued
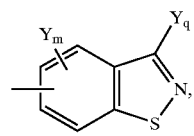 A-112
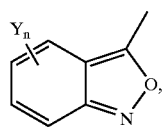 A-113
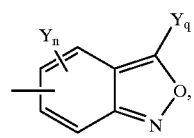 A-114
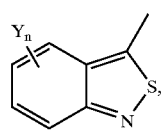 A-115
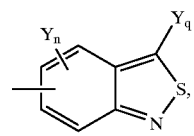 A-116
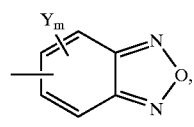 A-117
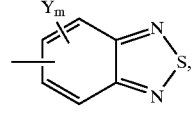 A-118
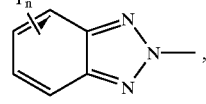 A-119
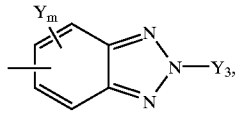 A-120
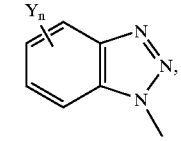 A-121
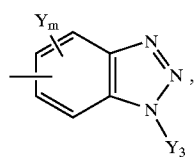 A-122
-continued
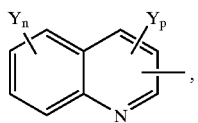 A-123
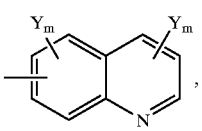 A-124
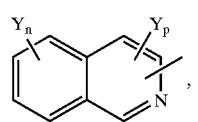 A-125
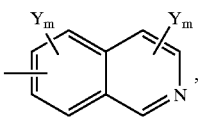 A-126
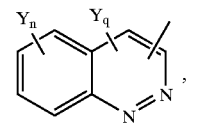 A-127
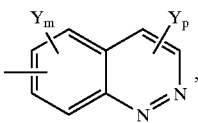 A-128
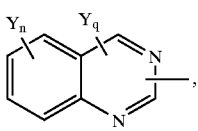 A-129
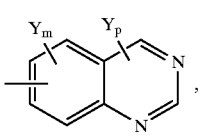 A-130
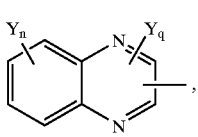 A-131
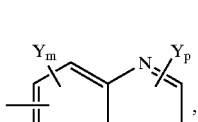 A-132
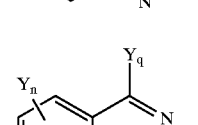 A-133
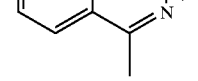

-continued

A-134 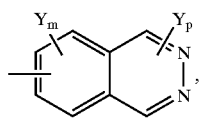

A-135 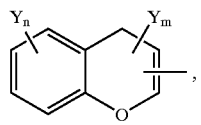

A-136 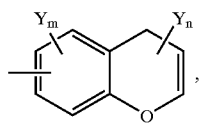

A-137 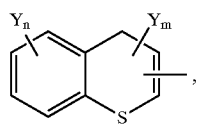

A-138 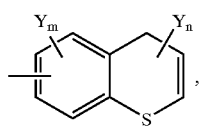

A-139 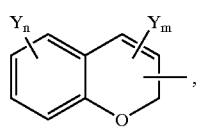

A-140 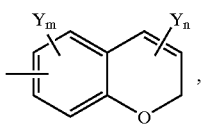

A-141 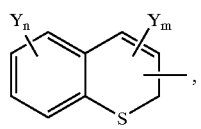

A-142 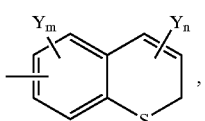

A-143 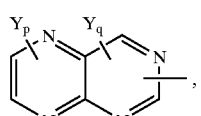

A-144 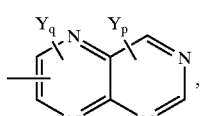

A-145 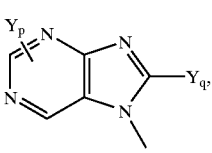

-continued

A-146 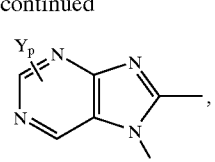

A-147 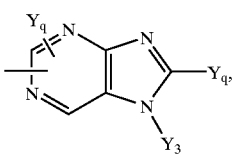

A-148 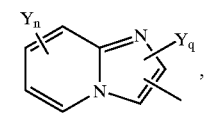

A-149 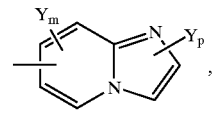

A-150 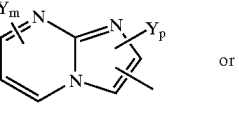

or

A-151

B is H, a $C_1$–$C_4$ alkyl, a $C_2$–$C_4$ alkoxyalkyl, $CH_2SCH_3$, $CH_2OC_2H_4OCH_3$, a $C_1$–$C_4$ alkyl substituted by Rc or Rd, a tetrahydropyranyl, $Si(CH_3)_3$, $SO_2Re$, $SO_2NHRb$, $SO_2NRaRb$, C(S)NHRb, C(S)NRaRb, $CH_2COORa$, C(O)Rf, P(O)RgRh, P(S)RgRh, an alkali metal, an alkaline earth metal or NHRiRjRk, X is one to three substituents as freely selected from a halogen, a $C_1$–$C_4$ alkyl, a $C_1$–$C_4$ haloalkyl, a $C_1$–$C_4$ alkoxy, a $C_1$–$C_4$ haloalkoxy, a $C_1$–$C_4$ alkylsulfenyl, a $C_1$–$C_4$ alkylsulfinyl, a $C_1$–$C_4$ alkylsulfonyl, a $C_1$–$C_4$ haloalkylsulfenyl, a $C_1$–$C_4$ haloalkylsulfinyl, a $C_1$–$C_4$ haloalkylsulfonyl, $NO_2$, CN, a phenyl and a phenoxy, Y, $Y_1$ and $Y_2$ are each independently of the other H, a halogen, a $C_1$–$C_4$ alkyl, a $C_1$–$C_4$ haloalkyl, a $C_1$–$C_4$ alkoxy, a $C_1$–$C_4$ haloalkoxy, a $C_1$–$C_4$ alkylsulfenyl, a $C_1$–$C_4$ alkylsulfinyl, a $C_1$–$C_4$ alkylsulfonyl, a $C_1$–$C_4$ haloalkylsulfenyl, a $C_1$–$C_4$ haloalkylsulfinyl, a $C_1$–$C_4$ haloalkylsulfonyl, $NO_2$ or CN, $Y_3$ is a $C_1$–$C_4$ alkyl or a $C_1$–$C_4$ haloalkyl, Ra is a $C_1$–$C_6$ alkyl, Rb is H, a $C_1$–$C_6$ alkyl, or a phenyl optionally substituted by $T^1$, Rc is a phenyl optionally substituted by one or more substituents as freely selected from a halogen, a $C_1$–$C_4$ alkyl, a $C_1$–$C_4$ alkoxy and a $C_1$–$C_4$ haloalkyl, Rd is a benzoyl optionally substituted by one or more substituents as freely selected from a halogen, a $C_1$–$C_4$ alkyl and a $C_1$–$C_4$ haloalkyl, Re is a $C_1$–$C_4$ alkyl, a $C_1$–$C_4$ haloalkyl, or a phenyl optionally substituted by $T^1$, Rf is a $C_1$–$C_6$ alkyl, a $C_2$–$C_6$ alkenyl, a $C_1$–$C_6$ haloalkyl, a $C_2$–$C_4$ alkoxyalkyl, a $C_3$–$C_6$ halocycloalkyl, a $C_1$–$C_4$ alkyl substituted by Rc, a $C_3$–$C_7$ cycloalkyl optionally substituted by a $C_1$–$C_4$ alkyl, a cycloalkyl substituted by Rc, a cyclopropyl substituted by Rc and a $C_1$–$C_4$ alkyl, a $C_3$–$C_4$ cycloalkyl substituted by Rc and a halogen, a cyclopropyl substituted by $T^2$ and a $C_1$–$C_4$ alkyl, a $C_2$–$C_4$ alkenyl substituted by Rc, a $C_1$–$C_6$ alkoxy, a $C_1$–$C_4$ haloalkoxy, a $C_2$–$C_5$ alkenyloxy, a $C_3$–$C_6$ cycloalkoxy optionally substituted by a $C_1$–$C_3$ alkyl, a benzyloxy, COORa, —$NU^1U^2$, a phenyl optionally substituted by $T^3$, a naphthyl, a pyridyl optionally substituted by $T^1$, a phenyl $C_1$–$C_6$ alkyl or A-1 to A-151, Rg and Rh are each independently of the other OH, a phenyl, a $C_1$–$C_6$ alkyl, a $C_1$–$C_6$ alkoxy or a $C_1$–$C_4$ alkylsulfenyl, Ri, Rj and Rk are each independently of the other H, a $C_1$–$C_6$ alkyl, a $C_1$–$C_4$ alkenyl, a $C_3$–$C_6$ cycloalkyl optionally substituted by a $C_1$–$C_3$ alkyl or a benzyl, or any two of Ri, Rj and Rk may, together with the nitrogen atom to which they are bonded, form a 5- to 8-membered ring group optionally containing an oxygen atom, a nitrogen atom or a sulfur atom, J is a pyrazolyl, an imidazolyl or a morpholinyl, $T^1$ is a halogen, a $C_1$–$C_4$ alkyl, a $C_1$–$C_4$ haloalkyl or a $C_1$–$C_4$ alkoxy, $T^2$ is a $C_2$–$C_4$ alkenyl optionally substituted by a halogen, $T^3$ is one to five substituents as freely selected from a halogen, a $C_1$–$C_4$ alkyl, a $C_1$–$C_4$ haloalkyl, a $C_1$–$C_4$ alkoxy, a $C_1$–$C_4$ haloalkoxy, a $C_1$–$C_4$ alkylsulfenyl, a $C_1$–$C_4$ alkylsulfinyl, a $C_1$–$C_4$ alkylsulfonyl, a $C_1$–$C_4$ haloalkylsulfenyl, a $C_1$–$C_4$ haloalkylsulfinyl, a $C_1$–$C_4$ haloalkylsulfonyl, $NO_2$, CN, CHO, —$NU^1U^2$, a phenyl and a phenoxy, $U^1$ and $U^2$ are each independently of the other H, a $C_1$–$C_6$ alkyl, COORa, a phenyl or a benzyl, or $U^1$ and $U^2$ may, together with the nitrogen atom to which they are bonded, form a 5- to 8-membered ring group optionally containing an oxygen atom, a nitrogen atom or a sulfur atom, m represents the number of substituents, and is 0, 1, 2 or 3, n represents the number of substituents, and is 0, 1, 2, 3 or 4, p represents the number of substituents, and is 0, 1 or 2, q represents the number of substituents, and is 0 or 1, (provided that when m, n or p is 2 or more, then the substituents may be the same or different)].

[2] Acrylonitrile compounds of the above-mentioned [1], in which A is

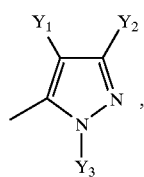
A-1

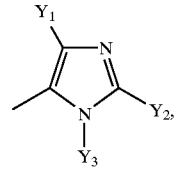
A-2

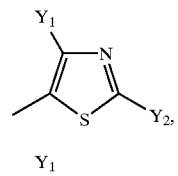
A-3

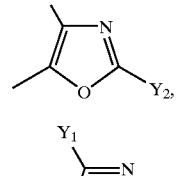
A-4

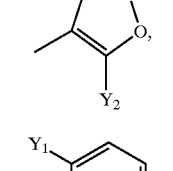
A-5

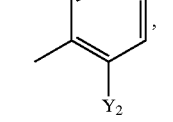
A-6

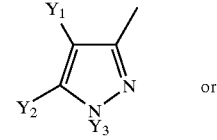
A-7 or

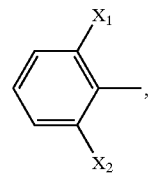
A-8

[3] Acrylonitrile compounds of the above-mentioned [2], in which R is 1-naphtyl, tertiary butyl or 2-pyridyl, $X_1$ is H, a halogen, a $C_1$–$C_4$ alkyl, a $C_1$–$C_4$ alkoxy, a $C_1$–$C_4$ haloalkyl or a phenyl, $X_2$ is H or a halogen, $R^1$ is H, a $C_1$–$C_6$ alkyl, a $C_3$–$C_7$ cycloalkyl, CN, COORa, CO(N-piperidyl), a $C_2$–$C_6$ alkylsulfenylalkyl, a $C_2$–$C_6$ alkoxyalkyl, $CH_3OC_2H_4OCH_2$, CONRaRb, a phenyl or $CH_2J$, A is A-1, A-2, A-3, A-6 or A-7, B is H, a $C_1$–$C_4$ alkyl, C(O)Rf, $SO_2$Re or a $C_2$–$C_4$ alkoxyalkyl, Ra and Rb are each independently of the other a $C_1$–$C_6$ alkyl, Rf is a $C_1$–$C_6$ alkyl, a $C_1$–$C_6$ alkoxy, a phenyl optionally substituted by a halogen, 2-pyridyl, 3-pyridyl, a phenyl $C_1$–$C_6$ alkyl or 5-pyrazolyl substituted by a $C_1$–$C_4$ alkyl, Re is a $C_1$–$C_4$ alkyl or a phenyl, $Y_1$ and $Y_2$ are each independently of the other H, a halogen, a $C_1$–$C_4$ alkyl, a $C_1$–$C_4$ haloalkyl or CN, $Y_3$ is a $C_1$–$C_4$ alkyl, J is an N-pyrazolyl or N-morpholinyl.

[4] Acrylonitrile compounds of the above-mentioned [3], in which R is

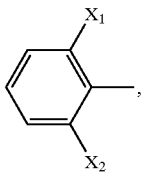

$X_1$ is H, a halogen, a $C_1$–$C_4$ alkyl, a $C_1$–$C_4$ alkoxy, a $C_1$–$C_4$ haloalkyl or a phenyl, $X_2$ is H or a halogen, $R^1$ is H, a $C_1$–$C_6$ alkyl, a $C_3$–$C_7$ cycloalkyl, CN, COORa, CO(N-piperidyl), a $C_2$–$C_6$ alkylsulfenylalkyl, a $C_2$–$C_6$ alkoxyalkyl, $CH_3OC_2H_4OCH_2$, CONRaRb, a phenyl or $CH_2J$, A is A-1, B is H, a $C_1$–$C_4$ alkyl, C(O)Rf, $SO_2$Re or a $C_2$–$C_4$ alkoxyalkyl, Ra and Rb are each independently of the other a $C_1$–$C_6$ alkyl, Rf is a $C_1$–$C_6$ alkyl, a $C_1$–$C_6$ alkoxy, a phenyl substituted by a halogen, 2-pyridyl, 3-pyridyl, a phenyl $C_1$–$C_6$ alkyl or 5-pyrazolyl substituted by a $C_1$–$C_4$ alkyl, Re is a $C_1$–$C_4$ alkyl or a phenyl, $Y_1$ is H, a halogen, a $C_1$–$C_4$ alkyl or CN, $Y_2$ is H, a halogen or a $C_1$–$C_4$ alkyl, $Y_3$ is a $C_1$–$C_4$ alkyl, J is an N-pyrazolyl or N-morpholinyl.

[5] Acrylonitrile compounds of the above-mentioned [4], in which $X_1$ is H, a fluorine atom, a chlorine atom, a bromine atom, methyl, methoxy, trifluoromethyl or a phenyl, $X_2$ is H, a fluorine atom or a chlorine atom, $R^1$ is H, methyl, ethyl, normal propyl, isopropyl, normal butyl, normal hexyl, cyclohexyl, CN, COORa, CO(N-piperidyl), methylsulfenylmethyl, methoxymethyl, ethoxymethyl, normal butoxymethyl, $CH_3OC_2H_4OCH_2$, CONRaRb, a phenyl, $CH_2$(N-pirazolyl) or $CH_2$(N-morpholinyl), B is H, methyl, C(O)Rf, $SO_2$Re, methoxymethyl or ethoxymethyl, Ra and Rb are methyl, Rf is tertiary butyl, ethoxy, isobutoxy, 2-chlorophenyl, 2-pyridyl, 3-pyridyl, benzyl, or 1,3,4-trimethyl-5-pyrazolyl, Re is methyl or phenyl, $Y_1$ is H, a chlorine atom, methyl or CN, $Y_2$ is H, a bromine atom, methyl or ethyl, $Y_3$ is methyl.

[6] Acrylonitrile compounds of the above-mentioned [4], in which $X_1$ is H, a halogen or a $C_1$–$C_4$ alkyl, $X_2$ is H or a halogen, $R^1$ is a $C_1$–$C_6$ alkyl, B is C(O)Rf, Rf is a $C_1$–$C_6$ alkyl, $Y_1$ is a halogen or a $C_1$–$C_4$ alkyl, $Y_2$ is a $C_1$–$C_4$ alkyl, $Y_3$ is a $C_1$–$C_4$ alkyl.

[7] Acrylonitrile compounds of the above-mentioned [6], in which $X_1$ is H, a fluorine atom, a chlorine atom, a bromine atom or methyl, $X_2$ is H or a fluorine atom, $R^1$ is methyl, ethyl, normal propyl, isopropyl or normal butyl, B is C(O)Rf, Rf is tertiary butyl, $Y_1$ is a chlorine atom or methyl, $Y_2$ is methyl, $Y_3$ is methyl.

[8] Acrylonitrile compounds of the above-mentioned [3], in which R is

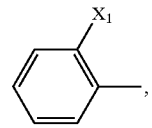

$X_1$ is H, a halogen or a $C_1$–$C_4$ alkyl, $R^1$ is H, a $C_1$–$C_6$ alkyl or a $C_3$–$C_7$ cycloalkyl, A is A-3, B is H or C(O)Rf, Rf is a $C_1$–$C_6$ alkyl, a phenyl or a phenyl $C_1$–$C_6$ alkyl, $Y_1$ is a $C_1$–$C_4$ alkyl or a $C_1$–$C_4$ haloalkyl, $Y_2$ is a $C_1$–$C_4$ alkyl.

[9] Acrylonitrile compounds of the above-mentioned [8], in which $X_1$ is H, a chlorine atom or methyl, $R^1$ is H, methyl, ethyl, isopropyl, normal butyl or cyclohexyl, B is H or C(O)Rf, Rf is tertiary butyl, a phenyl or a benzyl, $Y_1$ is methyl or trifluoromethyl, $Y_2$ is methyl.

[10] Acrylonitrile compounds of the above-mentioned [8], in which $X_1$ is H, $R^1$ is a $C_1$–$C_6$ alkyl, B is C(O)Rf, Rf is a $C_1$–$C_6$ alkyl, $Y_1$ is a $C_1$–$C_4$ alkyl, $Y_2$ is a $C_1$–$C_4$ alkyl.

[11] Acrylonitrile compounds of the above-mentioned [10], in which $X_1$ is H, $R^1$ is methyl, ethyl, isopropyl or normal butyl, B is C(O)Rf, Rf is tertiary butyl, $Y_1$ is methyl, $Y_2$ is methyl.

[12] An agricultural chemical characterized by comprising, as an active ingredient, one or more acrylonitrile compounds of any one of the above-mentioned [1] to [11].

The compounds of the above-mentioned [3] are preferable in the terms of excellent residual effect, the compounds of the above-mentioned [4] and [8] are more preferable, the compounds of the above-mentioned [5], [6], [9] and [10] are further more preferable, and the compounds of the above-mentioned [7] and [11] are the most preferable.

The moiety —C(CN)=C(OB) of the compounds (1) of the present invention includes two isomers of E-form and Z-form, both of which are within the scope of the present invention.

Now, preferred scopes of R, $R^1$, A, B, X, Y, Ra, Rb, Rc, Rd, Re, Rf, Rg, Rh, Ri, Rj, Rk, $T^1$, $T^3$, $Y_1$, $Y_2$, $Y_3$, $U^1$, $U^2$, m, n, p or q are referred to hereunder.

The preferred scope of R is the following group.
RI: $C_1$–$C_6$ alkyl, phenyl optionally substituted by X, pyridyl.
RII: $C_1$–$C_6$ alkyl, phenyl optionally substituted by X.

The preferred scope of $R^1$ is the following group.
$R^1$I: H, $C_1$–$C_6$ alkyl, $C_2$–$C_6$ alkoxyalkyl, $CH_3OC_2H_4OCH_2$, $C_2$–$C_6$ alkylsulfenylalkyl.
$R^1$II: H, $C_1$–$C_6$ alkyl.

The preferred scope of A is the following group.
AI: A-1, A-2, A-3, A-4, A-5, A-6, A-7, A-8.
AII: A-1, A-3, A-4, A-5, A-6, A-7, A-8.
AIII: A-1, A-3.

The preferred scope of B is the following group.
BI: H, $C_1$–$C_4$ alkyl, $C_2$–$C_4$ alkoxyalkyl, $CH_2OC_2H_4OCH_3$, $SO_2Re$, $SO_2NHRb$, $SO_2NRaRb$, C(S)NHRb, C(S)NRaRb, $CH_2COORa$, C(O)Rf, alkali metal, alkaline earth metal, NHRiRjRk.
BII: H, $C_1$–$C_4$ alkyl, $C_2$–$C_4$ alkoxyalkyl, $SO_2Re$, C(O)Rf, alkali metal, alkaline earth metal, NHRiRjRk.
BIII: H, $C_1$–$C_4$ alkyl, $C_2$–$C_4$ alkoxyalkyl, $SO_2Re$, C(O)Rf.

The preferred scope of X is the following group.
XI: one to three substituents as freely selected from halogen, $C_1$–$C_4$ alkyl, $C_1$–$C_4$ haloalkyl, $C_1$–$C_4$ alkoxy and phenyl.
XII: one to two substituents as freely selected from halogen, $C_1$–$C_4$ alkyl, $C_1$–$C_4$ haloalkyl, $C_1$–$C_4$ alkoxy and phenyl.

The preferred scope of Y is the following group.
YI: one to three substituents as freely selected from H, halogen, $C_1$–$C_4$ alkyl, $C_1$–$C_4$ haloalkyl, $C^1$–$C_4$ alkoxy, $C_1$–$C_4$ haloalkoxy, $C_1$–$C_4$ alkylsulfenyl, $C_1$–$C_4$ alkylsulfinyl, $C_1$–$C_4$ alkylsulfonyl, $C_1$–$C_4$ haloalkylsulfenyl, $C_1$–$C_4$ haloalkylsulfinyl, $C_1$–$C_4$ haloalkylsulfonyl and CN.
YII: one to three substituents as freely selected from H, halogen, $C_1$–$C_4$ alkyl and $C_1$–$C_4$ haloalkyl.

The preferred scope of Ra is the following group.
RaI: $C_1$–$C_4$ alkyl.

The preferred scope of Rb is the following group.
RbI: $C_1$–$C_6$ alkyl, phenyl optionally substituted by $T^1$.

The preferred scope of Rc is the following group.
RcI: halogen, $C_1$–$C_4$ alkyl, phenyl optionally substituted by $C_1$–$C_4$ alkoxy.

The preferred scope of Rd is the following group.
RdI: halogen, benzoyl optionally substituted by $C_1$–$C_4$ alkyl.

The preferred scope of Re is the following group.
ReI: $C_1$–$C_4$ alkyl, phenyl optionally substituted by $T^1$.

The preferred scope of Rf is the following group.
RfI: $C_1$–$C_6$ alkyl, $C_2$–$C_6$ alkenyl, $C_1$–$C_6$ haloalkyl, $C_2$–$C_4$ alkoxyalkyl, $C_3$–$C_6$ cycloalkyl optionally substituted by $C_1$–$C_3$ alkyl, $C_1$–$C_6$ alkoxy, $C_3$–$C_6$ cycloalkoxy, phenyl optionally substituted by $T^3$.
RfII: $C_1$–$C_6$ alkyl, $C_3$–$C_6$ cycloalkyl optionally substituted by $C_1$–$C_3$ alkyl, $C_1$–$C_6$ alkoxy, phenyl optionally substituted by $T^3$.

The preferred scope of Rg is the following group.
RgI: OH, phenyl, $C_1$–$C_6$ alkoxy, $C_1$–$C_4$ alkylsulfenyl.

The preferred scope of Rh is the following group.
RhI: $C_1$–$C_6$ alkoxy, $C_1$–$C_4$ alkylsulfenyl.

The preferred scope of Ri is the following group.
RiI: H, $C_1$–$C_6$ alkyl, $C_3$–$C_6$ cycloalkyl or benzyl, or Ri and Rj may, together with the nitrogen atom to which they are bonded, form a 5- to 6-membered ring group optionally containing an oxygen atom, a nitrogen atom or a sulfur atom.

The preferred scope of Rj is the following group.
RjI: H, $C_1$–$C_6$ alkyl, $C_3$–$C_6$ cycloalkyl or benzyl, or Ri and Rj may, together with the nitrogen atom to which they are bonded, form a 5- to 6-membered ring group optionally containing an oxygen atom, a nitrogen atom or a sulfur atom.

The preferred scope of Rk is the following group.
RkI: H, $C_1$–$C_6$ alkyl.

The preferred scope of $U^1$ is the following group.
$U^1$I: H, $C_1$–$C_6$ alkyl, COORa, phenyl or benzyl.

The preferred scope of $U^2$ is the following group.
$U^2$I: H, $C_1$–$C_6$ alkyl, COORa, phenyl or benzyl.

In addition, it is also preferable that $U^1$ and $U^2$ together with the nitrogen atom to which they are bonded, form a 5- to 8-membered ring group optionally containing an oxygen atom, a nitrogen atom or a sulfur atom.

The preferred scope of $T^1$ is the following group.
$T^1$I: halogen, $C_1$–$C_4$ alkyl, $C_1$–$C_4$ haloalkyl.

The preferred scope of $T^3$ is the following group.
$T^3$I: one to three substituents as freely selected from halogen, $C_1$–$C_4$ alkyl, $C_1$–$C_4$ haloalkyl, $C_1$–$C_4$ alkoxy, $C_1$–$C_4$ haloalkoxy, $C_1$–$C_4$ alkylsulfenyl, $C_1$–$C_4$ alkylsulfinyl, $C_1$–$C_4$ alkylsulfonyl, —$NU^1U^2$.
$T^3$II: one to three substituents as freely selected from halogen, $C_1$–$C_4$ alkyl, $C_1$–$C_4$ haloalkyl, $C_1$–$C_4$ alkoxy.

The preferred scope of $Y_1$ is the following group.
$Y_1$I: H, halogen, $C_1$–$C_4$ alkyl, $C_1$–$C_4$ haloalkyl.

The preferred scope of $Y_2$ is the following group.
$Y_2$I: H, halogen, $C_1$–$C_4$ alkyl, $C_1$–$C_4$ haloalkyl, $C_1$–$C_4$ alkoxy, $C_1$–$C_4$ haloalkoxy, $C_1$–$C_4$ alkylsulfenyl, $C_1$–$C_4$ alkylsulfinyl, $C_1$–$C_4$ alkylsulfonyl, $C_1$–$C_4$ haloalkylsulfenyl, $C_1$–$C_4$ haloalkylsulfinyl, $C_1$–$C_4$ haloalkylsulfonyl.
$Y_2$II: H, halogen, $C_1$–$C_4$ alkyl, $C_1$–$C_4$ haloalkyl.

The preferred scope of $Y_3$ is the following group.
$Y_3$I: $C_1$–$C_4$ alkyl.

The preferred scope of m is 1, 2 or 3, and more preferably is 1 or 2.

The preferred scope of n is 0, 1, 2 or 3, and more preferably is 1 or 2.

The preferred scope of p is 1 or 2.

The above-mentioned preferred groups in the scopes of the preferred substituents can be optionally combined. Hereunder mentioned are especially preferred compounds of the present invention.

Compounds of the invention comprising preferred substituents of RI, $R^1$I, AI, BI, XI, YI, RaI, RbI, ReI, RfI, RiI, RjI, RkI, $T^1$I, $T^3$I, $U^1$I, $U^2$I, $Y_1$I, $Y_2$I and $Y_3$I.

Compounds of the invention comprising preferred substituents of RI, $R^1$I, AII, BI, XI, RaI, RbI, ReI, RfI, RiI, RjI, RkI, $T^1$I, $T^3$I, $U^1$I, $U^2$I, $Y_1$I, $Y_2$I and $Y_3$I.

Compounds of the invention comprising preferred substituents of RI, $R^1$I, AIII, BI, XI, RaI, RbI, ReI, RfI, RiI, RjI, RkI, $T^1$I, $T^3$I, $U^1$I, $U^2$I, $Y_1$I, $Y_2$II and $Y_3$I.

Compounds of the invention comprising preferred substituents of RI, $R^1$I, AIII, BI, XI, RaI, RbI, ReI, RfI, RiI, RjI, RkI, $T^1$I, $T^3$I, $U^1$I, $U^2$1, $Y_1$I, $Y_2$II and $Y_3$I.

Compounds of the invention comprising preferred substituents of RII, R¹I, AI, BI, XI, YI, RaI, RbI, ReI, RfI, RiI, RjI, RkI, T¹I, T³I, U¹I, U²I, Y₁I, Y₂II and Y₃I.

Compounds of the invention comprising preferred substituents of RII, R¹I, AII, BI, XI, RaI, RbI, ReI, RfI, RiI, RjI, RkI, T¹I, T³I, U¹I, U²I, Y₁I, Y₂II and Y₃I.

Compounds of the invention comprising preferred substituents of RII, R¹I, AIII, BI, XI, RaI, RbI, ReI, RfI, RiI, RjI, RkI, T¹I, T³I, U¹I, U²I, Y₁I, Y₂II and Y₃I.

Compounds of the invention comprising preferred substituents of RI, R¹I, AII, BII, XI, RaI, RbI, ReI, RfI, RiI, RjI, RkI, T¹I, T³I, U¹I, U²I, Y₁I, Y₂II and Y₃I.

Compounds of the invention comprising preferred substituents of RI, R¹I, AII, BIII, XI, RaI, RbI, ReI, RfI, T¹I, T³I, U¹I, U²I, Y₁I, Y₂II and Y₃I.

Compounds of the invention comprising preferred substituents of RI, R¹I, AIII, BII, XI, RaI, RbI, ReI, RfI, RiI, RjI, RkI, T¹I, T³I, U¹I, U²I, Y₁I, Y₂II and Y₃I.

Compounds of the invention comprising preferred substituents of RI, R¹I, AIII, BIII, XI, RaI, RbI, ReI, RfI, T¹I, T³I, U¹I, U²I, Y₁I, Y₂II and Y₃I.

Compounds of the invention comprising preferred substituents of RII, R¹I, AII, BII, XI, RaI, RbI, ReI, RfI, RiI, RjI, RkI, T¹I, T³I, U¹I, U²I, Y₁I, Y₂II and Y₃I.

Compounds of the invention comprising preferred substituents of RII, R¹I, AII, BIII, XI, RaI, RbI, ReI, RfI, T¹I, T³I, U¹I, U²I, Y₁I, Y₂II and Y₃I.

Compounds of the invention comprising preferred substituents of RII, R¹I, AIII, BII, XI, RaI, RbI, ReI, RfI, RiI, RjI, RkI, T¹I, T³I, U¹I, U²I, Y₁I, Y₂II and Y₃I.

Compounds of the invention comprising preferred substituents of RII, R¹I, AIII, BIII, XI, RaI, RbI, ReI, RfI, T¹I, T³I, U¹I, U²I, Y₁I, Y₂II and Y₃I.

Compounds of the invention comprising preferred substituents of RI, R¹II, AII, BII, XI, RaI, RbI, ReI, RfI, RiI, RjI, RkI, T¹I, T³I, U¹, U²I, Y₁I, Y₂II and Y₃I.

Compounds of the invention comprising preferred substituents of RI, R¹II, AII, BIII, XI, RaI, RbI, ReI, RfI, T¹I, T³I, U¹I, U²I, Y₁I, Y₂II and Y₃I.

Compounds of the invention comprising preferred substituents of RI, R¹II, AIII, BII, XI, RaI, RbI, ReI, RfI, RiI, RjI, RkI, T¹I, T³I, U¹I, U²I, Y₁I, Y₂II and Y₃I.

Compounds of the invention comprising preferred substituents of RI, R¹II, AIII, BIII, XI, RaI, RbI, ReI, RfI, T¹I, T³I, U¹, U²I, Y₁, Y₂II and Y₃I.

Compounds of the invention comprising preferred substituents of RII, R¹II, AII, BII, XI, RaI, RbI, ReI, RfI, RiI, RjI, RkI, T¹I, T³I, U¹I, U²I, Y₁I, Y₂II and Y₃I.

Compounds of the invention comprising preferred substituents of RII, R¹II, AII, BIII, XI, RaI, RbI, ReI, RfI, T¹I, T³I, U¹I, U²I, Y₁I, Y₂II and Y₃I.

Compounds of the invention comprising preferred substituents of RII, R¹II, AIII, BII, XI, RaI, RbI, ReI, RfI, RiI, RjI, RkI, T¹I, T³I, U¹I, U²I, Y₁I, Y₂II and Y₃I.

Compounds of the invention comprising preferred substituents of RII, R¹II, AIII, BIII, XI, RaI, RbI, ReI, RfI, T¹I, T³I, U₁I, U²I, Y₁I, Y₂II and Y₃I.

Compounds of the invention comprising preferred substituents of RII, R¹I, AII, BII, XI, RaI, RbI, ReI, RfII, RiI, RjI, RkI, T¹I, T³I, U¹I, U²I, Y₁I, Y₂II and Y₃I.

Compounds of the invention comprising preferred substituents of RII, R¹I, AII, BIII, XI, RaI, RbI, ReI, RfII, T¹I, T³I, U¹I, U²I, Y₁I, Y₂II and Y₃I.

Compounds of the invention comprising preferred substituents of RII, R¹I, AIII, BII, XI, RaI, RbI, ReI, RfII, RiI, RjI, RkI, T¹I, T³I, U¹I, U²I, Y₁I, Y₂II and Y₃I.

Compounds of the invention comprising preferred substituents of RII, R¹I, AIII, BIII, XI, RaI, RbI, ReI, RfII, T¹I, T³I, U¹I, U²I, Y₁I, Y₂II and Y₃I.

Compounds of the invention comprising preferred substituents of RI, R¹II, AII, BII, XI, RaI, RbI, ReI, RfII, RiI, RjI, RkI, T¹I, T³I, U¹I, U²I, Y₁I, Y₂II and Y₃I.

Compounds of the invention comprising preferred substituents of RI, R¹II, AII, BIII, XI, RaI, RbI, ReI, RfII, T¹I, T³I, U¹I, U²I, Y₁I, Y₂II and Y₃I.

Compounds of the invention comprising preferred substituents of RI, R¹II, AIII, BII, XI, RaI, RbI, ReI, RfI, RiI, RjI, RkI, T¹I, T³I, U¹I, U²I, Y₁I, Y₂II and Y₃I.

Compounds of the invention comprising preferred substituents of RI, R¹II, AIII, BIII, XI, RaI, RbI, ReI, RfII, T¹I, T³I, U¹I, U²I, Y₁I, Y₂II and Y₃I.

Compounds of the invention comprising preferred substituents of RII, R¹II, AII, BII, XI, RaI, RbI, ReI, RfI, RiI, RjI, RkI, T¹I, T³I, U¹I, U²I, Y₁I, Y₂II and Y₃I.

Compounds of the invention comprising preferred substituents of RII, R¹II, AII, BIII, XI, RaI, RbI, ReI, RfII, RiI, RjI, RkI, T¹I, T³I, U¹I, U²I, Y₁I, Y₂II and Y₃I.

Compounds of the invention comprising preferred substituents of RII, R¹II, AIII, BII, XI, RaI, RbI, ReI, RfII, T¹I, T³I, U¹I, U²I, Y₁I, Y₂II and Y₃I.

Compounds of the invention comprising preferred substituents of RII, R¹II, AIII, BIII, XI, RaI, RbI, ReI, RfII, RiI, RjI, RkI, T¹I, T³I, U¹I, U²I, Y₁I, Y₂II and Y₃I.

Compounds of the invention comprising preferred substituents of RII, R¹I, AII, BII, XI, RaI, RbI, ReI, RfII, RiI, RjI, RkI, T¹I, T³II, U¹I, U²I, Y₁I, Y₂II and Y₃I.

Compounds of the invention comprising preferred substituents of RII, R¹I, AII, BIII, XI, RaI, RbI, ReI, RfII, T¹I, T³I, U¹I, U²I, Y₁I, Y₂II and Y₃I.

Compounds of the invention comprising preferred substituents of RII, R¹I, AIII, BII, XI, RaI, RbI, ReI, RfI, RiI, RjI, RkI, T¹I, T³II, U¹I, U²I, Y₁I, Y₂II and Y₃I.

Compounds of the invention comprising preferred substituents of RII, R¹I, AIII, BIII, XI, RaI, RbI, ReI, RfII, T¹I, T³II, U¹I, U²I, Y₁I, Y₂II and Y₃I.

Compounds of the invention comprising preferred substituents of RI, R¹II, AII, BII, XI, RaI, RbI, ReI, RfII, RiI, RjI, RkI, T¹I, T₃II, U¹I, U²I, Y₁I, Y₂II and Y₃I.

Compounds of the invention comprising preferred substituents of RI, R¹II, AII, BIII, XI, RaI, RbI, ReI, RfII, T¹I, T³II, U¹I, U²I, Y₁I, Y₂II and Y₃I.

Compounds of the invention comprising preferred substituents of RI, R¹II, AIII, BII, XI, RaI, RbI, ReI, RfII, RiI, RjI, RkI, T¹I, T³II, U¹I, U²I, Y₁I, Y₂II and Y₃I.

Compounds of the invention comprising preferred substituents of RI, R¹II, AIII, BIII, XI, RaI, RbI, ReI, RfII, T¹I, T³II, U¹I, U²I, Y₁I, Y₂II and Y₃I.

Compounds of the invention comprising preferred substituents of RII, R¹II, AII, BII, XI, RaI, RbI, ReI, RfI, RiI, RjI, RkI, T¹I, T³II, U¹I, U²I, Y₁I, Y₂II and Y₃I.

Compounds of the invention comprising preferred substituents of RII, R¹II, AII, BIII, XI, RaI, RbI, ReI, RfII, T¹I, T³II, U¹I, U²I, Y₁I, Y₂II and Y₃I.

Compounds of the invention comprising preferred substituents of RII, R¹II, AIII, BII, XI, RaI, RbI, ReI, RfII, RiI, RjI, RkI, T¹I, T³II, U¹I, U²I, Y₁I, Y₂II and Y₃I.

Compounds of the invention comprising preferred substituents of RII, R¹II, AIII, BIII, XI, RaI, RbI, ReI, RfII, T¹I, T³II, U¹I, U²I, Y₁I, Y₂II and Y₃I.

Now, specific examples of atoms and groups in the definitions of R, R¹, A, B, X, Y, Ra, Rb, Rc, Rd, Re, Rf, Rg, Rh, Ri, Rj, Rk, T¹, T², T³, Y₁, Y₂, Y₃, U¹ and U² are mentioned below.

The halogen atom for R¹, X, Y, Rc, Rd, T¹, T², T³, Y₁ and Y₂ includes a fluorine atom, a chlorine atom, a bromine atom and an iodine atom. Preferred are a fluorine atom, a chlorine atom and a bromine atom.

The alkyl for R, $R^1$, B, X, Y, Ra, Rb, Rc, Rd, Re, Rf, Rg, Rh, Ri, Rj, Rk, $T^1$, $T^3$, $Y_1$, $Y_2$, $Y_3$, $U^1$ and $U^2$ may be a straight chain or branched alkyl group having indicated carbon atoms, which includes, for example, methyl, ethyl, n-propyl, isopropyl, n-butyl, isobutyl, tert-butyl, sec-butyl, pentyl-1, pentyl-2, pentyl-3, 2-methylbutyl-1, 2-methylbutyl-2, 2-methylbutyl-3, 3-methylbutyl-1, 2,2-dimethylpropyl-1, hexyl-1, hexyl-2, hexyl-3, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, etc.

The haloalkyl for $R^1$, X, Y, Rc, Rd, Re, Rf, $T^1$, $T^3$, $Y_1$, $Y_2$ and $Y_3$ may be a straight chain or branched haloalkyl group having indicated carbon atoms, which includes, for example, fluoromethyl, chloromethyl, bromomethyl, fluoroethyl, chloroethyl, bromoethyl, fluoro-n-propyl, chloro-n-propyl, difluoromethyl, chlorodifluoromethyl, trifluoromethyl, dichloromethyl, trichloromethyl, difluoroethyl, trifluoroethyl, trichloroethyl, chlorodifluoromethyl, bromodifluoromethyl, trifluorochloroethyl, hexafluoro-n-propyl, chlorobutyl and fluorobutyl, etc.

The $C_3$–$C_7$ cycloalkyl optionally substituted by a $C_1$–$C_4$ alkyl for R, Rf, Ri, Rj and Rk includes, for example, cyclopropyl, 1-methylcyclopropyl, 2,2,3,3-tetramethylcyclopropyl, cyclobutyl, 1-ethylcyclobutyl, 1-n-butylcyclobutyl, cyclopentyl, 1-methylcyclopentyl, cyclohexyl, 1-methylcyclohexyl and 4-methylcyclohexyl, cycloheptyl, etc.

The $C_1$–$C_4$ alkyl optionally substituted by Rc for Rf includes, for example, benzyl, 2-chlorobenzyl, 3-bromobenzyl, 4-chlorobenzyl, 4-methylbenzyl, 4-tertiary butylbenzyl, 2-methylbenzyl, 2-methoxybenzyl, 1-phenylethyl, 1-(3-chlorophenyl)ethyl, 2-phenylethyl, 1-methyl-1-phenylethyl, 1-(4-chlorophenyl)-1-methylethyl, 1-(3-chlorophenyl)-1-methylethyl, 1-phenylpropyl, 2-phenylpropyl, 3-phenylpropyl, 1-phenylbutyl, 2-phenylbutyl, 3-phenylbutyl, 4-phenylbutyl, 1-methyl-1-phenylpropyl, 1-methyl-2-phenylpropyl, 1-methyl-3-phenylpropyl, 2-methyl-2-phenylpropyl, 2-(4-chlorophenyl)-2-methylpropyl and 2-methyl-2-(3-methylphenyl)propyl, etc.

The phenyl optionally substituted by $T^1$ for Rb and Re includes, for example, phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 4-iodophenyl, 2,4-dichlorophenyl, 3,4-dichlorophenyl, 2,6-difluorophenyl, 2,6-dichlorophenyl, 2-fluoro-4-chlorophenyl, 2,3,4,5,6-pentafluorophenyl, 2-methylphenyl, 3-methylphenyl, 4-methylphenyl, 2,5-dimethylphenyl, 4-methyl-2,3,5,6-tetrafluorophenyl, 2-methoxyphenyl, 3-methoxyphenyl, 4-methoxyphenyl, 2,6-methoxyphenyl, 3,4-dimethoxyphenyl and 3,4,5-trimethoxyphenyl, 2-trifluoromethylphenyl, 3-trifluoromethylphenyl, 4-trifluoromethylphenyl, etc.

The alkoxy for $R^1$, X, Y, Rc, Rf, Rg, Rh, $T^1$, $T^3$, $Y_1$ and $Y_2$ may be a straight chain or branched alkoxy having indicated carbon atoms, which includes, for example, methoxy, ethoxy, n-propoxy, isopropoxy, n-butoxy, isobutoxy, sec-butoxy, isobutoxy, sec-butoxy, tert-butoxy, n-pentyloxy, 1-methylbutyloxy, 2-methylbutyloxy, 3-methylbutyloxy, 1,1-dimethylpropoxy, 1,2-dimethylpropoxy, 2,2-dimethylpropoxy, 1-ethylpropyloxy, n-hexyloxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropyloxy, 1,2,2-trimethylpropyloxy, 1-ethyl-1-methylpropyloxy and 1-ethyl-2-methylpropyloxy, etc.

The —$NU^1U^2$ for Rf and $T^3$ includes, for example, methylamino, ethylamino, n-propylamino, isopropylamino, n-butylamino, isobutylamino, sec-butylamino, tert-butylamino, n-pentylamino, 1-methylbutylamino, 2-methylbutylamino, 3-methylbutylamino, 1,1-dimethylpropylamino, 1,2-dimethylpropylamino, 2,2-dimethylpropylamino, 1-ethylpropylamino, n-hexylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino, dimethylamino, diethylamino, di-n-propylamino, diisopropylamino, di-n-butylamino, di-sec-butylamino, diisobutylamino, di-n-pentylamino, di-n-hexylamino, methylethylamino, methylpropylamino, methylisopropylamino, methylbutylamino, methyl-sec-butylamino, methylisobutylamino, methyl-tert-butylamino, methylpentylamino, methylhexylamino, ethylpropylamino, ethylisopropylamino, ethylbutylamino, ethyl-sec-butylamino, ethylisobutylamino, ethylpentylamino, ethylhexylamino, phenylamino, benzylamino, N-acetamide, N-ethylacetamide, N-phenylacetamide and N-acetacetamide, etc., to which is applied the indicated scope of the carbon atoms constituting it.

The haloalkoxy for X, Y, Rf, $T^3$, $Y_1$ and $Y_2$ may be a straight chain or branched haloalkoxy, which includes, for example, fluoromethoxy, difluoromethoxy, trifluoromethoxy, chlorodifluoromethoxy, bromodifluoromethoxy, dichlorofluoromethoxy, chloromethoxy, dichloromethoxy, trichloromethoxy, bromomethoxy, fluoroethoxy, chloroethoxy, bromoethoxy, difluoroethoxy, trifluoroethoxy, tetrafluoroethoxy, pentafluoroethoxy, trichloroethoxy, trifluorochloroethoxy, fluoropropoxy, chloropropoxy, bromopropoxy, fluorobutoxy, chlorobutoxy, fluoro-iso-propoxy, chloro-iso-propoxy, etc.

The $C_1$–$C_4$ alkylsulfenyl for X, Y, Rg, Rh, $T^3$, $Y_1$ and $Y_2$ includes, for example, methylthio, ethylthio, n-propylthio, iso-propylthio, n-butylthio, iso-butylthio, sec-butylthio and tert-butylthio, etc.

The $C_1$–$C_4$ alkylsulfinyl for X, Y, $T^3$, $Y_1$ and $Y_2$ includes, for example, methylsulfinyl, ethylsulfinyl, n-propylsulfinyl, iso-propylsulfinyl, n-butylsulfinyl, iso-butylsulfinyl, sec-butylsulfinyl and tert-butylsulfinyl, etc.

The $C_1$–$C_4$ alkylsulfonyl for X, Y, $T^3$, $Y_1$ and $Y_2$ includes, for example, methyl sulfonyl, ethylsulfonyl, n-propylsulfonyl, iso-propylsulfonyl, n-butylsulfonyl, iso-butylsulfonyl, sec-butylsulfonyl and tert-butylsulfonyl, etc.

The $C_2$–$C_4$ alkoxyalkyl for $R^1$, B and Rf includes, for example, methoxymethyl, ethoxymethyl, n-propoxymethyl, i-propoxymethyl, n-butoxymethyl, i-butoxymethyl, s-butoxymethyl, t-butoxymethyl, n-pentyloxymethyl, methoxyethyl, ethoxymethyl and methoxypropyl, etc., to which is applied the indicated scope of the carbon atoms constituting it.

The $C_2$–$C_6$ alkylsulfenylalkyl for $R^1$ includes, for example, methylthiomethyl, ethylthiomethyl, n-propylthiomethyl, i-propylthiomethyl, n-butylthiomethyl, i-butylthiomethyl, s-butylthiomethyl, t-butylthiomethyl, n-pentylthiomethyl, methylthioethyl, ethylthiomethyl and methylthiopropyl, etc.

The naphthyl for R and Rf includes, for example, 1-naphtyl and 2-naphtyl.

The haloalkylsulfenyl for X, Y, $T^3$, $Y_1$ and $Y_2$ may be a straight chain or branched $C_1$–$C_4$ haloalkylthio, including, for example, fluoromethylthio, chlorodifluoromethylthio, bromodifluoromethylthio, trifluoromethylthio, trichloromethylthio, 2,2,2-trifluoroethylthio, 1,1,2,2-tetrafluoroethylthio, fluoroethylthio, pentafluoroethylthio and fluoro-iso-propylthio, etc.

The haloalkylsulfinyl for X, Y, $T^3$, $Y_1$ and $Y_2$ may be a straight chain or branched $C_1$–$C_4$ haloalkylsulfinyl, including, for example, fluoromethylsulfinyl, chlorodifluoromethylsulfinyl, bromodifluoromethylsulfinyl, trifluoromethylsulfinyl, trichloromethylsulfinyl, 2,2,2-trifluoroethylsulfinyl, 1,1,2,2-tetrafluoroethylsulfinyl, fluoroethylsulfinyl, pentafluoroethylsulfinyl and fluoro-iso-propylsulfinyl, etc.

The haloalkylsulfonyl for X, Y, $T^3$, $Y_1$ and $Y_2$ may be a straight chain or branched $C_1$–$C_4$ haloalkylsulfonyl, including, for example, fluoromethylsulfonyl, chlorodifluoromethylsulfonyl, bromodifluoromethylsulfonyl, trifluoromethylsulfonyl, trichloromethylsulfonyl, 2,2,2-trifluoroethylsulfonyl, 1,1,2,2-tetrafluoroethylsulfonyl, fluoroethylsulfonyl, pentafluoroethylsulfonyl and fluoro-iso-propylsulfonyl, etc.

The alkenyloxy for Rf may be a straight chain or branched $C_2$–$C_4$ alkenyloxy, including, for example, allyloxy, 2-propenyloxy, 2-butenyloxy and 2-methyl-2-propenyloxy, etc.

The $C_1$–$C_4$ alkenyl for Ri, Rj and Rk includes, for example, allyl, 2-propenyl, 2-butenyl, 2-methyl-2-propenyl, 4-methyl-3-pentenyl and 2-hexenyl, etc, to which is applied the indicated scope of the carbon atoms constituting it.

The alkali metal for B includes, for example, lithium, sodium and potassium.

The alkaline earth metal for B includes, for example, magnesium, calcium, strontium or barium, preferably magnesium, calcium or barium.

The NHRiRjRk for B includes, for example, asmmonium group, monomethylammonium group, dimethylammonium group, trimethylammonium group, diethylammonium group, triethylammonium group, diisopropylammonium group, diisopropylethylammonium group, hexylmethylammonium group, cyclopropylmethylammonium group, cyclohexylmethylammonium group, allylmethylammonium group, benzylmethylammonium group or 4-methylcyclohexylethylammonium group, or any two of Ri, Rj and Rk together with the nitrogen atom to which they are bonded, form a heterocyclic 5-, 6-, 7- or 8-membered ammonium group optionally containing an oxygen atom, a nitrogen atom or a sulfur atom.

For Ri, Rj and Rk, the heterocyclic 5- to 8-membered ammonium group optionally containing an oxygen atom, a nitrogen atom or a sulfur atom, which is formed by any two of Ri, Rj and Rk together with the nitrogen atom to which they are bonded, includes, for example, pyrrolidine, pyrazolidine, imidazolidine, oxazolidine, isoxazolidine, thiazolidine, piperidine, piprerazine, morpholine, thiamorpholine, hexamethyleneimine and heptamethylenimine, etc.

For $U^1$ and $U^2$, the heterocyclic 5- to 8-membered ring optionally containing an oxygen atom, a nitrogen atom or a sulfur atom, which is formed by $U^1$ and $U^2$ together with the nitrogen atom to which they are bonded, includes, for example, pyrrolidine, pyrazolidine, imidazolidine, oxazolidine, isoxazolidine, thiazolidine, piperidine, piprerazine, morpholine, thiamorpholine, hexamethyleneimine and heptamethylenimine, etc.

The $C_3$–$C_6$ halocycloalkyl for Rf includes, for example, fluorocyclopropyl, difluorocyclopropyl, chlorocyclopropyl, dichlorocyclopropyl, 1-methyl-2,2-dichlorocyclopropyl, chlorocyclobutyl, dichlorocyclobutyl, chlorocyclopentyl, dichlorocyclopentyl, chlorocyclohexyl, dichlorocyclohexyl and tetrafluorocyclobutyl, etc.

The cyclopropyl optionally substituted by $T^2$ and $C_1$–$C_4$ alkyl for Rf includes, for example, 2,2-dimethyl-3-(2,2-dimethylethenyl)cyclopropyl, 3-(2,2-dibromoethenyl)-2,2-dimethylcyclopropyl, 3-(2,2-dichloroethenyl)-2,2-dimethylcyclopropyl and 3-(2,2-chlorotrifluoroetheny)-2,2-dimethylcyclopropyl, etc.

The $C_3$–$C_6$ cycloalkoxy optionally substituted by $C_1$–$C_4$ alkyl for Rf includes, for example, cyclopropoxy, cyclobutoxy, cyclopentoxy, cyclohexyloxy, 1-methylcyclopropoxy, etc.

The $C_3$–$C_4$ cycloalkyl substituted by Rc and halogen atom for Rf includes, for example, 2,2-dichloro-1-phenylcyclopropyl, 2,2-dichloro-1-(3-chlorophenyl) cyclopropyl, 2,2-dichloro-1-(4-methoxyphenyl) cyclopropyl, 2,2-dichloro-1-(4-ethoxyphenyl)cyclopropyl, 2,2-dichloro-1-(4-i-propyloxyphenyl)cyclopropyl, 2,2-dichloro-1-(4-t-butylphenyl)cyclopropyl, 2,2-dichloro-1-(4-methoxyphenyl)-3-phenylcyclopropyl and 1-(4-ethoxyphenyl)-2,2,3,3-tetrafluorobutyl, etc.

The cyclopropyl substituted by Rc and $C_1$–$C_4$ alkyl for Rf includes, for example, 2,2-dimethyl-1-phenylcyclopropyl, 1-(4-chlorophenyl)-2,2-dimethylcyclopropyl, 2,2-dimethyl-3-phenylcyclopropyl, 3-(3-chloropheny)-2,2-dimethylcyclopropyl, (4-chlorophenyl)-2,2-dimethyl-3-phenylcyclopropyl, (4-bromophenyl)-2,2-dimethyl-3-phenylcyclopropyl, 2,2-dimethyl-3-(4-methylphenyl) cyclopropyl and (4-tertiary butylphenyl)-2,2-dimethyl-3-phenylcyclopropyl, etc.

The $C_3$–$C_6$ cycloalkyl substituted by Rc for Rf includes, for example, 1-phenylcyclopropyl, 1-(3-chlorophenyl) cyclopropyl, 1-(4-chlorophenyl)cyclopropyl, 1-(4-bromophenyl)cyclopropyl, 1-(4-fluorophenyl)cyclopropyl, 1-(4-ethylphenyl)cyclopropyl, 1-(4-propylphenyl) cyclopropyl, 2-phenylcyclopropyl, 1-phenylcyclobutyl, 2-phenylcyclobutyl, 1-phenylcyclopentyl, 1-(4-chlorophenyl)cyclopentyl, 3-phenylcyclopentyl, 1-phenylcyclohexyl, 1-(3-fluorophenyl)cyclohexyl, 1-(4-chlorophenyl)cyclohexyl, 1-(4-tertiary butylphenyl) cyclohexyl, 2-phenylcyclohexyl, 3-phenylcyclohexyl and 4-phenylcyclohexyl, etc.

Even at low concentration, the compounds of the present invention effectively prevent various pests, which include, for example, so-called agricultural insect pests that injure agricultural and horticultural crops and trees, so-called livestock insects that live on livestock and poultry, so-called sanitary insect pests that have various negative influences on the human living environment including houses, so-called stored products pests that injure grains stored in storehouses, and also acarids, nematodes, molluscs and crustaceans that live in the same sites as above and injure those mentioned above.

Examples of the insect pests, acarids, nematodes, molluscs and crustaceans capable of being exterminated by the compounds of the present invention are mentioned below, which, however, are not limitative.

Insect pests of Lepidoptera, such as rice stem borer (*Chilo suppressalis*), rice leafroller (*Cnaphalocrocis medinalis*), green rice catapillar (*Neranga aenescens*), rice skipper (*Pamara guttata*), diamond back moths (*Plutella xylostella*), cabbage armyworms (*Mamestra brassicae*), common white (*Pieris rapae cnucivora*), turnip moth (*Agrotis segetum*), common cutworm (*Spodptera litura*), beet armyworm (*Spodptera exigua*), tabacco budwarm (*Helicoverpa armigera*), smaller tea tortrix (Adoxophyes sp.), oriental tea tortrix (*Homona magnanima*), peach fruit moth (*Carposina niponensis*), oriental fruit moth (*Grapholita molesta*), summer fruit tortrix (*Adoxophyes orana fasciata*), apple leafminers (*Phyllonorycter ringoniella*), corn earwarm (*Helicoverpa zea*), tobacco budworm (*Heliothis virescens*), European corn borer (*Ostrinia nubialis*), fall armyworm (*Spodoptera frugiperda*), Coding moth (*Cydia pomonella*), fall webworms (*Hyphantria cunea*), etc.:

Insect pestd of Hemiptera, such as green rice leafhopper (*Nephotettix cincticeps*), brown rice planthoppers (*Nilaparvata lugens*), green peach aphid (*Myzus persicae*), cotton aphid (*Aphis gossypii*), greenhouse whitefly (*Trialeurodes vaporariorum*), sweetpotato white fly (*Bemisia tabaci*), pear psylla (*Psylla pyricola*), azalea lace bug (*Stephantis pyriodes*), arrowhead scale (*Unaspis yanonensis*), comstock mealybug (*Pseudococcus comstocki*), red wax scale (*Ceroplastes rubens*), giant mealybug (*Drosicha corpulenta*), brown-marmorated stinkbug (*Halyomorpha mista*), cabbage bug (*Eurydema rugosam*), bed bug (*Cimex lectularis*), etc.;

Insect pests of Coleoptera, such as twenty-eight-spotted ladybird (*Henosepilachna vigintioctopunctata*), cupreous chafers (*Anomala cuprea*), Japanese beetle (*Popilla japonica*), ricewater weevil (*Lissorhoptrus oryzophilus*), hunting billbug (*Sphenophrus venatus vestitus*), sweetpotato weevil (*Cylas formicarius*), cucurbit leaf beetle (*Aulacophora femoralis*), striped flea beetle (*Phyllotreta striolata*), Colorado potato beetle (*Leptinotarsa decemlineata*), white-spotted longicorn beetle (*Anoplophora malasiaca*), Paederus fuscipes, pine sawyers (*Monochamus altematus*), sugarcane wire worm (*Melanotus tamsuyensis*), Europea domina, corn rootworms (Diabrotica spp.), lesser rice weevil (*Sitophilus oryzae*), granary weevils (*Sitophilus granarius*), red four beetle (*Tribolium castaneum*), etc.;

Insect pests of Diptera, such as legume leafminer (*Liriomyza trifoli*), seedcorn maggot (*Delia platura*), Hessia fly (*Mayetiola destructor*), melon fly (*Dacus (Zengodacus) cucurbitae*), Mediterranear fruit fly (*Ceratitis capitata*), house flies (*Musca domestica*), stable fly (*Stomoxys calcitrans*), sheep ked (*Melophagus orinus*), common cattle grub (*Hypoderm lineatum*), nothern cattle grub (*Hypoderma boris*), sheep boffly (*Oestrus ovis*), tsetse fly (*Golossina palpais*), *Prosimulium yezoensis, Tabanus trigonus*, bath room fly (*Telmatoscopus albipunctatus*), *Leptoconops nipponensis*, common gnat (*Culex pipiens pallens*), yellow-fever mosquitoes (*Aedes aegypti*), *Aëdes albopictus, Anopheles culicifacies*, etc.;

Insect pests of Hymenoptera, such as cabbage sawfly (*Athalis rosae ruficornis*), pine sawfly (*Neodiprion sertifer*), chestnut sawfly (*Apethymust kuri*), soldier ant, *Camponotus japonicus*, giant hornet (*Vespa mandarina*), bulldog ant, fire ant, pharaoh ant, etc.;

Insect pests of Thysanoptera, such as melon thrips (*Thrips palmi*), onion thrips (*Thrips tabaci*), western flower thrips (*Frankliniella occidentalis*), flower thrips (*Frankliniella intonsa*), yellow tea thrip (*Scirtothrips dorsalis*), etc.; Insect pests of Dictyoptera, such as smokybrown cockroach (*Periplaneta fuliginosa*), Japanese cockroach (*Periplaneta japonica*), German cockroach (*Blattella germanica*), etc.;

Insect pests of Orthoptera, such as African mole cricket (*Gryllotalpa africana*), field cricket (*Teleogryllus emma*), oriental migratory locust (*Locusta migratoria*), rice grasshopper (*Oxya yezoensis*), desert locust (*Schistocerca gregaria*), etc.; Insect pests of Isoptera, such as Formosan subterranean termit (*Coptotermes formosanus*), Reticulitermes (Leucotermes) speratus, *Odontotermes formosanus*, etc.;

Insect pests of Siphonaptera, such as fleas (*Ctenocephalides felis*), human fleas (*Pulex irritans*), oriental rat flea (*Xenopsylla cheopis*), etc.;

Insect pestd of Mallophaga, such as Chicken bodylouse (*Menacanthus stramineus*), cattle biting louse (*Bovicola bovis*), etc.;

Insect of pests of Anoplura, such as short-nosed cattle louse (*Haematopinus eurystemus*), hog louse (*Haematopinus suis*), long-nosed cattle louse (*Linognathus vituli*), little cattle louse (*Solenopotes capillatus*), etc.;

Pests of THYSANURA, such as oriental siverfish (*Ctenolepisma villosa*), etc.,;

Pests of PSOCOPTERA, such as *Liposcelis bostrychophilus*, etc.;

Pests of COLLEMBOLA, such as *Onychiuras pseudarmatus* yagii, ONYCHIURIDAE, etc.,;

Pests of TETRANYCHIDAE, such as citrus red mite (*Panonychus citn*), European red mite (*Panonychus ulmi*), two-spotted spider mite (*Tetranychus urticae*), Kanzawa spider mite (*Tetranychus kanzawal*), etc.;

ests of ERIOPHYDAE, such as pink citrus rust mite (*Aculops pelekassi*), pear rust mite (*Epitrimerus pyri*), dry bulb mite (*Aceria tulipae*), pink tea mite (*Acaphylla theae*), etc.;

Pests of TARSONEMIDAE, such as broad mites (*Polyphagotarsonemus latus*), cyclamen mite, strawberry mite (*Steneotarsonemus pallidus*), etc.;

Pests of ACARIDAE, such as mold mite, copra mite, forage mite (*Tyrophagus putrescetiae*), bulb mite (*Rhizoglyphus robini*), etc.;

Pests of VARROIDAE, such as bee brood mite (*Varroa jacobsoni*), etc.;

Pests of Ixodide, such as bull ticks (*Boophilus mivroplus*), *Haemaphysalis Iongicornis*, etc.;

Pests of Sarcoptidae, such as sarcoptes mange mite (*Sarcaptes scabiei Linné*), etc.

Pests of Chilopodera, such as *Sclopendra subspinipes japonica, Thereuronema hilgendorfi*, etc.,;

Pests of Diplopoda, such as hot house millipede (*Oxidus gracilis*), etc.,;

Nematodes, such as southern root-knot nematodae (*Meloidogyne incognita*), northern root-knot nematodae (*Meloidogyne hapla*), Cobb root-lesion nematode (*Pratylenchus penetraus*), walnut root-lesion nematode (*Pratylenchus vulnus*), potato cyst nematode (*Globodera rostochiensis*), pine wood nematode (*Bursaphelenchus xylophilus*), etc.;

Mollusca, such as apple snali (*Pomacea canaliculta*), *Incilaria pilineata*, giant African snail (*Achatina fulica*), *Acusta despecta sieboldiana, Euhadra peliomphala*, pillbug (*Armadilliduim vulgara*), etc.;

Crustaceans, such as pilibug (*Armadilliduim vulgara*), etc.

That is, the compounds of the present invention can effectively prevent insect pests including Orthoptera, Hemiptera, Lepidoptera, Coleoptera, Hymenoptera, Diptera and Isoptera as well as acari and lice, and disease damage to plants at low concentration. On the other hand, the compounds of the present invention include very useful compounds that have little adverse effect on mammals, fishes, crustaceans and beneficial insects.

The compounds (1) of the present invention can be produced according to the following methods indicated in Scheme 1. That is, the compounds (1) of the present invention can be produced by reacting a cyanomethyltriazole derivative of general formula (2) with a carboxylic acid derivative of general formula (3) in the presence of a base to partially give the aimed compounds, then the resulting compound is reacted with a compound of general formula (4) to obtain the compound of present invention. The compounds of general formula (4) are concretely acyl halides, benzoyl halides, alkyl halides, benzyl halides, alkoxyalkyl halides, alkoxyalkoxyalkyl halides, phenoxyalkyl halides, benzyloxyalkyl halides, alkylsulfonates, benzene sulfonates, toluene sulfonates, α-haloketones and α-haloesters, and the like.

[Scheme 1]

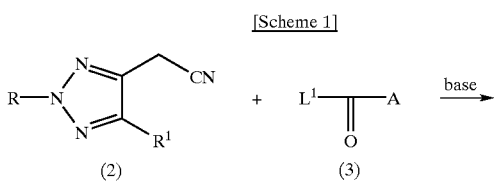

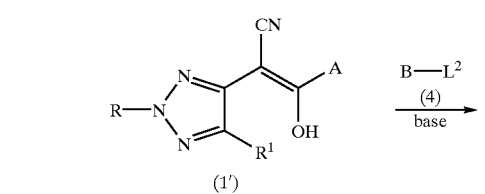

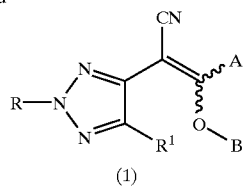

(1)

[In Scheme 1, R, $R^1$, A and B have the same meanings as defined above; $L^1$ and $L^2$ are a suitable leaving group, such as a chlorine atom, a bromine atom, an iodine atom, a $C_1$–$C_4$ alkylsulfonyloxy, a benzenesulfonyloxy, a toluenesulfonyloxy, 1-imidazolyl or 1-pyrazolyl.]

In some cases of the above-mentioned methods, it is preferable to use a base. The base includes, for example, alkali metal alkoxides such as sodium ethoxide, sodium methoxide, potassium t-butoxide, etc., alkali metal hydroxides such as sodium hydroxide, potassium hydroxide, etc., alkali metal carbonates such as sodium carbonate, potassium carbonate, etc., organic bases such as triethylamine, pyridine, DBU, etc., organic lithium compounds such as butyl lithium, etc., lithium amides such as lithium diisopropylamide, lithium bistrimethylsilylamide, etc., and sodium hydride, and so on.

The reactions described above may be effected in a solvent that is inert to the reaction. The solvent includes, for example, lower alcohols such as methanol, ethanol, etc., aromatic hydrocarbons such as benzene, toluene, etc., ethers such as diethyl ether, tetrahydrofuran, 1,4-dioxane, 1,2-dimethoxyethane, 1,2-diethoxyethane, etc., ketones such as acetone, methyl ethyl ketone, methyl isobutyl ketone, etc., halogenated hydrocarbons such as methylene chloride, chloroform, 1,2-dichloroethane, etc., amides such as dimethylformamide, dimethylacetamide, 1,3-dimethylimidazolidinone, etc., nitrites such as acetonitrile, etc., dimethylsulfoxide, and mixed solvents of these. As the case may be, a quaternary ammonium salt such as tetra-n-butylammonium bromide may be added to the reaction system as a catalyst to obtain good results. The reaction temperature may be freely settled within a range between −70° C. and 200° C. When the reaction temperature falls between 0° C. and 150° C. or a solvent is used, the temperature preferably ranges from −70° C. to the boiling point of the solvent. The base may be used in an amount of from 0.05 to 10 equivalents, preferably from 0.05 to 3 equivalents, of the reaction substrate.

The cyanomethyltriazole derivatives of general formula (2) may be synthesized according to a method such as the method of Scheme 2.

[Scheme 2]

Method A

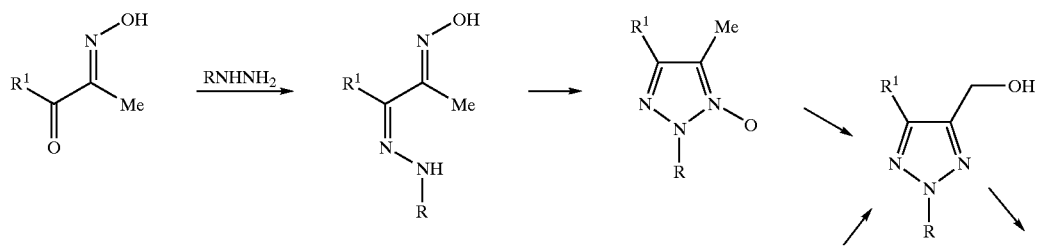

Method B

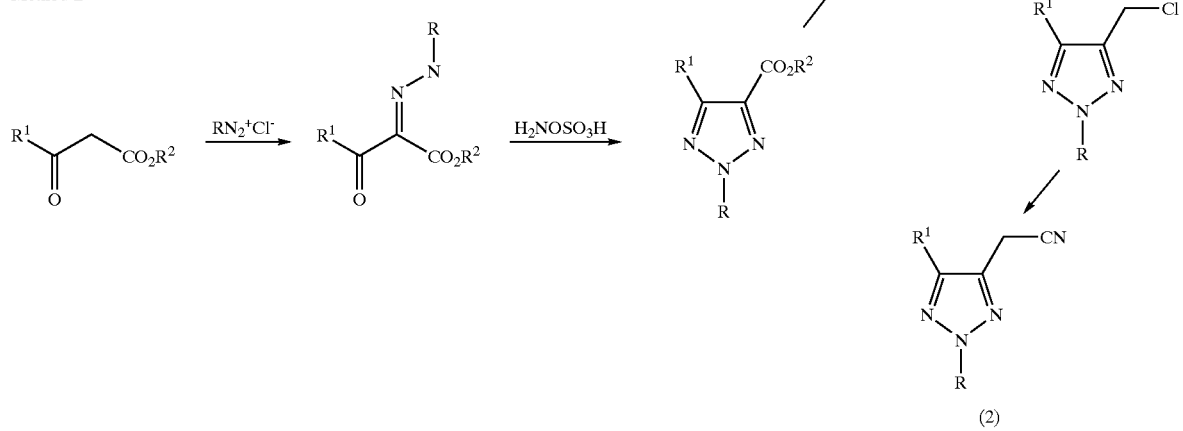

[In Scheme 2, R and $R^1$ have the same meanings as defined above; $R^2$ is a lower alkyl.]

The compounds of the present invention may be obtained from reaction mixtures according to any ordinary methods. If the purification of the compounds of the invention is needed, they can be separated and purified by any ordinary methods of, for example, recrystallization or column chromatography.

Of the compounds of the invention, those having an asymmetric carbon atom include optically active compounds of (+) form and (−) form.

Examples of the compounds of the present invention are shown in Tables 1 and 2 below. The abbreviations in these tables are as follows: Me: methyl group, Et: ethyl group, Pr: propyl group, Bu: butyl group, Pen: pentyl group, Hex: hexyl group, Hep: heptyl group, Oct: octyl group, Non: nonyl group, Dec: decyl group, Ph: phenyl group, n: normal, i: iso, sec: secondary, t: tertiary, c: cyclo.

TABLE 1

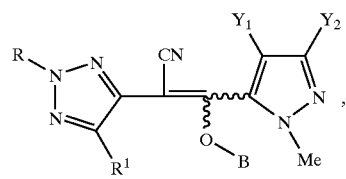

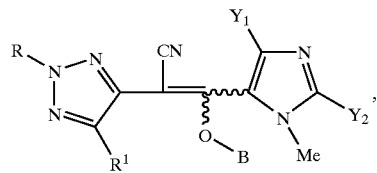

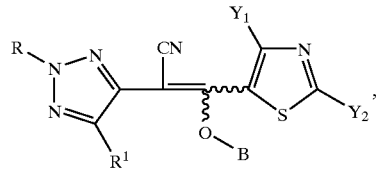

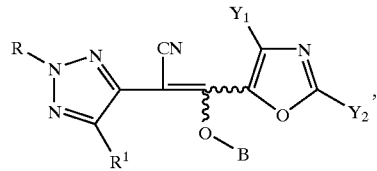

TABLE 1-continued

[Structures showing triazole compounds connected via C(CN)=C(OB) linker to: isoxazole, phenyl, pyrazole, or isothiazole rings with Y₁ and Y₂ substituents]

| R | R¹ | B | Y₁ | Y₂ |
|---|---|---|---|---|
| Me | H | H | H | H |
| Et | Me | CH₂SMe | Me | H |
| nPr | Me | SO₂NHMe | H | Me |
| iPr | Me | SO₂NMe₂ | Cl | Cl |
| nBu | Me | CSNHEt | H | CF₃ |
| iBu | Me | CSNMe₂ | Me | MeO |
| sBu | Me | CH₂COOEt | Me | CF₃O |
| tBu | Me | COtBu | H | Me |
| tBu | Me | COtBu | Me | H |
| tBu | Me | COtBu | Me | Me |
| tBu | Me | COtBu | Cl | Me |
| tBu | Me | COtBu | Me | Cl |
| tBu | Me | COtBu | Me | Br |
| tBu | Me | COtBu | CF₃ | Me |
| tBu | Me | COtBu | F | H |
| tBu | Me | COtBu | F | F |
| tBu | Me | COOMe | Me | Me |
| tBu | Me | COOiBu | Me | Me |
| tBu | Me | CO(2-Cl—Ph) | H | Me |
| tBu | Me | SO₂Ph | Me | Me |
| tBu | Me | Me | Cl | Me |
| tBu | Me | CH₂OEt | Cl | Et |
| tBu | Et | COtBu | Me | Et |
| tBu | nPr | COtBu | H | Me |
| tBu | iPr | COtBu | Me | Me |
| tBu | nBu | COtBu | Cl | Me |
| tBu | nPen | COOMe | Cl | Et |
| tBu | nHex | COOiBu | Me | Et |
| tBu | CN | CO(2-Cl—Ph) | H | Me |
| tBu | COOMe | SO₂Ph | Me | Me |
| tBu | OMe | Me | Cl | Me |
| tBu | OnHex | CH₂OEt | Cl | Et |
| nPen | NO₂ | COtBu | Me | Et |
| nHex | COMe | COtBu | H | Me |
| cPr | Ph | COtBu | Me | Me |
| cPen | CH₂Ph | COtBu | H | Me |
| cHex | H | COtBu | Me | Me |
| cHex | Me | COtBu | Cl | Me |
| cHex | Me | COtBu | Cl | Et |
| cHex | H | COtBu | Me | Et |
| cHex | Me | Me | Me | H |

TABLE 1-continued

| | | | | |
|---|---|---|---|---|
| cHex | Me | CH$_2$OEt | CF$_3$ | Me |
| cHep | Me | COtBu | Me | Me |
| cHep | Me | COtBu | H | Me |
| cHep | Me | COtBu | Cl | Me |
| cHep | nBu | H | Me | Me |
| Ph | H | H | CF$_3$ | Me |
| Ph | H | COtBu | Me | Me |
| Ph | H | COtBu | H | Me |
| Ph | H | COtBu | Cl | Me |
| Ph | H | COtBu | Cl | H |
| Ph | H | COtBu | F | H |
| Ph | H | COtBu | F | F |
| Ph | H | COtBu | Cl | Et |
| Ph | Me | COtBu | Cl | Et |
| Ph | Me | COtBu | Cl | nPr |
| Ph | Me | COtBu | Cl | nBu |
| Ph | Me | COtBu | Me | Et |
| Ph | Me | COtBu | Me | CF$_3$ |
| Ph | Me | COtBu | Cl | Cl |
| Ph | Me | COtBu | Cl | H |
| Ph | Me | COtBu | Br | H |
| Ph | Me | COtBu | Me | H |
| Ph | Me | COtBu | Me | Br |
| Ph | Me | COtBu | Me | Cl |
| Ph | Me | COMe | H | Me |
| Ph | Me | COCH=CH$_2$ | Me | Me |
| Ph | Me | COCH=CMe$_2$ | Cl | Me |
| Ph | Me | COCF$_3$ | Cl | Et |
| Ph | Me | COCF$_2$CF$_3$ | Me | Et |
| Ph | Me | COCH$_2$OMe | Me | H |
| Ph | Me | CO(2,2-F$_2$-cPr) | CF$_3$ | Me |
| Ph | Me | COOCH$_2$CH$_2$Cl | H | Me |
| Ph | Me | COOCH$_2$CMe=CH$_2$ | Me | Me |
| Ph | Me | COcPr | Cl | Me |
| Ph | Me | CO(1-Me-cPr) | Cl | Et |
| Ph | Me | COcHex | Me | Et |
| Ph | Me | CO(1-Me-cHex) | Me | H |
| Ph | Me | COOcPen | CF$_3$ | Me |
| Ph | Me | COOCH$_2$Ph | H | Me |
| Ph | Me | COCOOMe | Me | Me |
| Ph | Me | CONHMe | Cl | Me |
| Ph | Me | CONHPh | Cl | Et |
| Ph | Me | CON(COMe)Me | Me | Et |
| Ph | Me | CON(COOMe)Et | Me | H |
| Ph | Me | CONMe$_2$ | CF$_3$ | Me |
| Ph | Me | CONMePh | H | Me |
| Ph | Me | CONMeCH$_2$Ph | Me | Me |
| Ph | Me | COPh | Cl | Me |
| Ph | Me | CO(2-Cl—Ph) | Cl | Et |
| Ph | Me | CO(2-Me—Ph) | Me | Et |
| Ph | Me | CO(2-CF$_3$—Ph) | Me | H |
| Ph | Me | CO(2-MeO—Ph) | CF$_3$ | Me |
| Ph | Me | CO(2-CHF$_2$O—Ph) | H | Me |
| Ph | Me | CO(2-MeS—Ph) | Me | Me |
| Ph | Me | CO(2-MeSO—Ph) | CF$_3$S | Me |
| Ph | Me | CO(2-MeSO$_2$Ph) | CF$_3$SO | Et |
| Ph | Me | CO(2-CF$_3$S—Ph) | CF$_3$SO$_2$ | Et |
| Ph | Me | CO(2-CBrF$_2$SO—Ph) | Me | H |
| Ph | Me | CO(2-CHF$_2$SO$_2$—Ph) | CF$_3$ | Me |
| Ph | Me | CO(3-NO$_2$—Ph) | H | Me |
| Ph | Me | CO(4-CN—Ph) | Me | Me |
| Ph | Me | CO(4-NMe$_2$—Ph) | Cl | Me |
| Ph | Me | CO(2,6-F$_2$—Ph) | Cl | Et |
| Ph | Me | CO(2,6-Cl$_2$—Ph) | Me | Et |
| Ph | Me | CO(3,4-(MeO)$_2$—Ph) | Me | H |
| Ph | Me | CO(2,4,6-Me$_3$—Ph) | CF$_3$ | Me |
| Ph | Me | CO(1-naphthyl) | H | Me |
| Ph | Me | CO(2-pyridinyl) | Me | Me |
| Ph | Me | CO(3-pyridinyl) | Cl | Me |
| Ph | Me | CO(4-pyridinyl) | Cl | Et |
| Ph | Et | CO(2,6-F$_2$—Ph) | H | Me |
| Ph | Et | COtBu | Cl | Et |
| Ph | Et | COtBu | Cl | H |
| Ph | Et | COtBu | Br | H |
| Ph | Et | COtBu | NO$_2$ | Me |
| Ph | nPr | COtBu | Me | Me |
| Ph | iPr | COtBu | Cl | Me |
| Ph | nBu | COtBu | Cl | Et |
| Ph | iBu | COtBu | CF$_3$ | Me |

TABLE 1-continued

| | | | | |
|---|---|---|---|---|
| Ph | sBu | COtBu | Me | H |
| Ph | nPen | COtBu | Me | Br |
| Ph | nHex | COtBu | Cl | Et |
| Ph | CN | COtBu | Me | Me |
| Ph | CO$_2$Me | COtBu | Cl | Me |
| Ph | CO$_2$Et | COtBu | Cl | Et |
| Ph | CO$_2$nPr | COtBu | CF$_3$ | Me |
| Ph | CO$_2$nBu | COtBu | Me | H |
| Ph | CO$_2$nPen | COtBu | Me | Br |
| Ph | CO$_2$nHex | COtBu | H | Me |
| Ph | CONH$_2$ | COtBu | Me | Me |
| Ph | CONHMe | COtBu | Cl | Me |
| Ph | CONHEt | COtBu | Cl | Et |
| Ph | CONHnPr | COtBu | CF$_3$ | Me |
| Ph | CONHiPr | COtBu | Me | H |
| Ph | CONHnBu | COtBu | Me | Br |
| Ph | CONHPh | COtBu | H | Me |
| Ph | CONMe$_2$ | COtBu | Me | Me |
| Ph | CONMeEt | COtBu | Cl | Me |
| Ph | CONEt$_2$ | COtBu | Cl | Et |
| Ph | CONMePh | COtBu | CF$_3$ | Me |
| Ph | CONEtPh | COtBu | Me | H |
| Ph | CONMe(2-Cl—Ph) | COtBu | Me | Br |
| Ph | CONMe(4-CF$_3$—Ph) | COtBu | H | Me |
| Ph | CONMe(3-Me—Ph) | COtBu | Me | Me |
| Ph | CONEt(3,4-(MeO)$_2$Ph) | COtBu | Cl | Me |
| Ph | OMe | COtBu | Cl | Et |
| Ph | OEt | COtBu | CF$_3$ | Me |
| Ph | OnPr | COtBu | Me | H |
| Ph | OiPo | COtBu | Me | Br |
| Ph | OnBu | COtBu | H | Me |
| Ph | OiBu | COtBu | Me | Me |
| Ph | OsBu | COtBu | Cl | Me |
| Ph | OtBu | COtBu | Cl | Et |
| Ph | OnPen | COtBu | CF$_3$ | Me |
| Ph | OCH$_2$tBu | COtBu | Me | H |
| Ph | OnHex | COtBu | Me | Br |
| Ph | CH$_2$OMe | COtBu | H | Me |
| Ph | CH$_2$OnPr | COtBu | Cl | Me |
| Ph | CH$_2$OiPr | COtBu | Cl | Et |
| Ph | CH$_2$OnBu | COtBu | CF$_3$ | Me |
| Ph | CH$_2$OnPen | COtBu | Me | H |
| Ph | CH$_2$SMe | COtBu | Me | Br |
| Ph | CH$_2$SEt | COtBu | H | Me |
| Ph | CH$_2$SnPr | COtBu | Me | Me |
| Ph | CH$_2$SiPr | COtBu | Cl | Me |
| Ph | CH$_2$SnBu | COtBu | Cl | Et |
| Ph | CH$_2$SiBu | COtBu | CF$_3$ | Me |
| Ph | CH$_2$SnPen | COtBu | Me | H |
| Ph | Cl | CH$_2$OC$_2$H$_4$OMe | Me | Br |
| Ph | Br | CH$_2$Ph | H | Me |
| Ph | I | C$_2$H$_4$Ph | Me | Me |
| Ph | CF$_3$ | CH$_2$COPh | Cl | Me |
| Ph | CClF$_2$ | SiMe$_3$ | Cl | Et |
| Ph | CF$_2$CF$_3$ | SO$_2$Me | CF$_3$ | Me |
| Ph | Me | PO(OMe)$_2$ | Me | H |
| Ph | Me | PS(OEt)$_2$ | Me | Br |
| Ph | Me | Na | H | Me |
| Ph | Me | K | Me | Me |
| Ph | Me | NHEt$_3$ | Cl | Me |
| Ph | Me | NH(—(CH$_2$)$_4$—) | Cl | Et |
| Ph | Me | NH(—(CH$_2$)$_5$—) | CF$_3$ | Me |
| Ph | Me | NH(—(CH$_2$)$_6$—) | Me | Me |
| Ph | Me | NH(—(CH$_2$)$_7$—) | Me | Me |
| Ph | Me | NH(—CH$_2$H$_4$OC$_2$H$_4$—) | H | Me |
| 2-F—Ph | H | COtBu | Me | H |
| 2-F—Ph | Me | COtBu | Me | Br |
| 2-F—Ph | Me | COtBu | H | Me |
| 2-F—Ph | Me | COtBu | Me | Me |
| 2-F—Ph | Me | COtBu | Cl | Me |
| 2-F—Ph | Me | COtBu | Cl | Et |
| 2-F—Ph | Me | COtBu | CF$_3$ | Me |
| 2-F—Ph | H | H | Me | Me |
| 2-F—Ph | Me | H | Me | Me |
| 2-Cl—Ph | H | COtBu | Me | H |
| 2-Cl—Ph | Me | COtBu | Me | Br |
| 2-Cl—Ph | Me | COtBu | H | Me |
| 2-Cl—Ph | Me | COtBu | Me | Me |
| 2-Cl—Ph | Me | COtBu | Cl | Me |

TABLE 1-continued

| | | | | |
|---|---|---|---|---|
| 2-Cl—Ph | Me | COtBu | Cl | Et |
| 2-Cl—Ph | Me | COtBu | $CF_3$ | Me |
| 2-Cl—Ph | Et | COtBu | Me | Me |
| 2-Cl—Ph | $CO_2Me$ | COtBu | Me | Me |
| 2-Br—Ph | H | COtBu | Me | H |
| 2-Br—Ph | Me | COtBu | Me | Br |
| 2-Br—Ph | Me | COtBu | H | Me |
| 2-Br—Ph | Me | COtBu | Me | Me |
| 2-Br—Ph | Me | COtBu | Cl | Me |
| 2-Br—Ph | Me | COtBu | Cl | Et |
| 2-Br—Ph | Me | COtBu | $CF_3$ | Me |
| 2-Me—Ph | Me | COtBu | Me | H |
| 2-Et—Ph | Me | COtBu | Me | Br |
| 2-$CF_3$—Ph | Me | COtBu | H | Me |
| 2-MeO—Ph | Me | COtBu | Me | Me |
| 2-$CHF_2O$—Ph | Me | COtBu | Cl | Me |
| 2-MeS—Ph | Me | COtBu | Cl | Et |
| 2-EtSO—Ph | Me | COtBu | $CF_3$ | Me |
| 2-n$PrSO_2$—Ph | Me | COtBu | Me | H |
| 2-$CF_3$S—Ph | Me | COtBu | Me | Br |
| 2-$CF_3$SO—Ph | Me | COtBu | H | Me |
| 2-$CF_3SO_2$—Ph | Me | COtBu | Me | Me |
| 2-$NO_2$—Ph | Me | COtBu | Cl | Me |
| 2-CN—Ph | Me | COtBu | Cl | Et |
| 2-Ph—Ph | Me | COtBu | $CF_3$ | Me |
| 2-PhO—Ph | Me | COtBu | Me | Me |
| 2,3-$Cl_2$—Ph | H | COtBu | Me | H |
| 2,6-$F_2$—Ph | Me | COtBu | Me | Br |
| 2,6-$F_2$—Ph | Me | COtBu | H | Me |
| 2,6-$F_2$—Ph | Me | COtBu | Me | Me |
| 2,6-$F_2$—Ph | Me | COtBu | Cl | Me |
| 2,6-$F_2$—Ph | Me | COtBu | Cl | Et |
| 2,6-$F_2$—Ph | Me | COtBu | $CF_3$ | Me |
| 2,6-$F_2$—Ph | Me | $CO_2Me$ | Me | H |
| 2,6-$F_2$—Ph | Et | Me | H | Me |
| 2,6-$F_2$—Ph | CN | CO(2-Cl—Ph) | Cl | Me |
| 2,6-$F_2$—Ph | $CO_2Et$ | COcHex | Me | Me |
| 2,6-$F_2$—Ph | OnBu | $SO_2CF_3$ | H | Me |
| 2,6-$Cl_2$-4-$CF_3$—Ph | Me | COtBu | Me | Me |
| 1-naphthyl | H | COtBu | $CF_3$ | Me |
| 2-naphthyl | Br | COtBu | Me | H |
| 2-pyridyl | $CF_3$ | COtBu | H | Me |
| 3-pyridyl | COOnPen | COtBu | Cl | Me |
| 4-pyridyl | COMe | COtBu | Me | Me |
| 2-pyridyl | H | H | Me | Me |
| 2-pyridyl | H | COtBu | Me | Me |
| 2-pyridyl | Me | H | Me | Me |
| 2-pyridyl | Me | COtBu | Me | Me |
| 2-pyridyl | iPr | H | Me | Me |
| 2-pyridyl | iPr | COtBu | Me | Me |
| Ph | $CH_2OEt$ | H | Me | Me |
| Ph | $CH_2OEt$ | COtBu | Me | Me |
| Ph | $CH_2OnPr$ | H | Me | Me |
| Ph | $CH_2OnPr$ | COtBu | Me | Me |
| Ph | $CH_2OiPr$ | H | Me | Me |
| Ph | $CH_2OiPr$ | COtBu | Me | Me |
| Ph | $CH_2OnBu$ | H | Me | Me |
| Ph | $CH_2OnBu$ | COtBu | Me | Me |
| Ph | $CH_2OPh$ | H | Me | Me |
| Ph | $CH_2OPh$ | COtBu | Me | Me |

TABLE 2

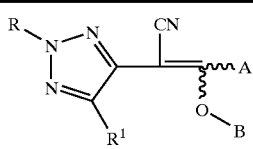

| R | $R^1$ | B | A | $Y_1$ | $Y_3$ |
|---|---|---|---|---|---|
| Ph | Me | H | A-9 | 3-Cl | — |
| Ph | Me | COtBu | A-9 | 3-Cl | — |
| Ph | Me | COtBu | A-9 | 3-Me | — |

TABLE 2-continued

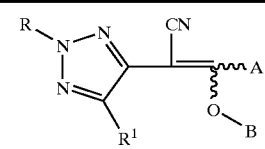

| R | $R^1$ | B | A | $Y_1$ | $Y_3$ |
|---|---|---|---|---|---|
| Ph | Me | COtBu | A-9 | 3,4-$Cl_2$ | — |
| Ph | Et | COtBu | A-10 | 4-OMe | — |
| Ph | Et | COtBu | A-10 | 4-OMe-5-Cl | — |

TABLE 2-continued

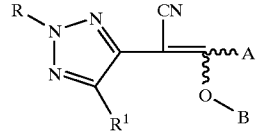

| R | R¹ | B | A | Y₁ | Y₃ |
|---|----|---|---|----|----|
| Ph | Me | COtBu | A-11 | 3-Cl | — |
| Ph | Me | COtBu | A-12 | 4-Cl | — |
| tBu | H | COtBu | A-13 | 2-Cl | — |
| Ph | Me | COtBu | A-14 | 3-Me | Me |
| Ph | iPr | COtBu | A-15 | 2-Me | Me |
| Ph | Me | COtBu | A-16 | 4-Me | — |
| Ph | Me | COtBu | A-17 | 2-Cl | — |
| Ph | Me | COtBu | A-18 | 4-Me | — |
| Ph | Me | COtBu | A-19 | 2-Cl | — |
| Ph | Me | COtBu | A-20 | — | — |
| Ph | Me | COtBu | A-21 | 4-Me | Me |
| Ph | Me | COtBu | A-22 | 2-Me | Me |
| Ph | Me | COtBu | A-23 | 4-Me | — |
| Ph | Me | COtBu | A-24 | 3-Me-4-Cl | — |
| Ph | Et | COtBu | A-25 | 4-Cl | — |
| Ph | Et | COtBu | A-26 | 3-Me-4-Cl | — |
| Ph | nHex | COtBu | A-27 | 3,5-Me₂ | — |
| Ph | CN | COtBu | A-28 | Me | — |
| Ph | CO₂Me | COtBu | A-29 | Me | — |
| Ph | OMe | COtBu | A-30 | Me | — |
| Ph | OnHex | COtBu | A-31 | Me | — |
| Ph | NO₂ | COtBu | A-32 | Me | — |
| Ph | COMe | COtBu | A-33 | Me | — |
| Ph | Me | COtBu | A-34 | 3,5-Me₂ | — |
| Ph | Me | COtBu | A-35 | 5-Me | Me |
| Ph | Me | COtBu | A-36 | 3-Me | Me |
| Ph | Et | COtBu | A-36 | 3-Me | Me |
| Ph | Me | COtBu | A-37 | Me | Me |
| Ph | Me | COtBu | A-38 | 3-Me | — |
| Ph | Me | COtBu | A-39 | Me | — |
| Ph | Me | COtBu | A-40 | Me | — |
| Ph | Me | COtBu | A-41 | 5-Me | — |
| Ph | Me | COtBu | A-42 | 5-Me | — |
| Ph | Me | COtBu | A-43 | Me | Me |
| Ph | Me | COtBu | A-44 | Me | Me |
| Ph | Me | COtBu | A-45 | Me | Me |
| Ph | Me | COtBu | A-46 | Me | — |
| Ph | Me | COtBu | A-47 | Me | — |
| Ph | Me | COtBu | A-48 | — | Me |
| Ph | Me | COtBu | A-49 | — | Me |
| Ph | Me | COtBu | A-50 | — | — |
| Ph | Me | COtBu | A-51 | 5-CF₃ | — |
| Ph | Me | COtBu | A-52 | 4-CF₃ | — |
| Ph | Me | COtBu | A-53 | 3-Me | — |
| Ph | Me | COtBu | A-54 | 4-Me | — |
| Ph | Me | COtBu | A-55 | 3-Me | — |
| Ph | Me | COtBu | A-56 | 4-Me | — |
| Ph | Me | COtBu | A-57 | 5-Me | — |
| Ph | Me | COtBu | A-58 | 3-Me | — |
| Ph | Me | COtBu | A-59 | 4-Me | — |
| Ph | Me | COtBu | A-60 | 3,5-Me₂ | — |
| Ph | Me | COtBu | A-61 | 4-Cl | Me |
| Ph | Me | COtBu | A-62 | 3-Me | Me |
| Ph | Me | COtBu | A-63 | 3-Me | Me |
| Ph | Me | COtBu | A-64 | 2-Cl | — |
| Ph | Me | COtBu | A-65 | 3-Me | Me |
| Ph | Me | COtBu | A-66 | 2,4-Me₂ | Me |
| Ph | Me | COtBu | A-67 | 2,5-Me₂ | Me |
| Ph | Me | COtBu | A-68 | 4-Me | Me |
| Ph | Me | COtBu | A-69 | Me | — |
| Ph | Me | COtBu | A-70 | Me | — |
| Ph | Me | COtBu | A-71 | Me | — |
| Ph | Me | COtBu | A-72 | Me | — |
| Ph | Me | COtBu | A-73 (2-yl) | 4-Me | — |
| Ph | Me | COtBu | A-74 (2-yl) | 4-Me | — |
| Ph | Me | COtBu | A-75 (2-yl) | 4-Me | Me |
| Ph | Me | COtBu | A-76 (2-yl) | 4-Me | — |
| Ph | Me | COtBu | A-77 (2-yl) | 4-Me | — |
| Ph | Me | COtBu | A-78 (2-yl) | 4-Me | Me |
| Ph | Me | COtBu | A-79 (3-yl) | 4-Me | — |
| Ph | Me | COtBu | A-80 (3-yl) | 4-Me | Me |
| Ph | Me | COtBu | A-81 (3-yl) | 4-Me | Me |
| Ph | Me | COtBu | A-82 (3-yl) | 4-Me | — |
| Ph | Me | COtBu | A-83 (3-yl) | 4-Me | Me |
| Ph | Me | COtBu | A-84 (3-yl) | 4-Me | Me |
| Ph | Me | COtBu | A-85 (2-yl) | 4,5-Cl₂ | — |
| Ph | Me | COtBu | A-86 (4-yl) | 5-Cl | Me |
| Ph | Me | COtBu | A-87 | 4-Me | — |
| Ph | Me | COtBu | A-88 (6-yl) | 2-Me | — |
| Ph | Me | COtBu | A-89 | 4-Me | — |
| Ph | Me | COtBu | A-90 (6-yl) | 2-Me | — |
| Ph | Me | COtBu | A-91 | 2-Me | — |
| Ph | Me | COtBu | A-92 | — | Me |
| Ph | Me | COtBu | A-93 (5-yl) | 6-NO₂ | Me |
| Ph | Me | COtBu | A-94 | 3-Me | — |
| Ph | Me | COtBu | A-95 | — | Me |
| Ph | Me | COtBu | A-96 | — | Me |
| Ph | Me | COtBu | A-97 (4-yl) | 3-Me | Me |
| Ph | Me | COtBu | A-98 (2-yl) | 3-Me | — |
| Ph | Me | COtBu | A-99 (4-yl) | — | — |
| Ph | Me | COtBu | A-100 (2-yl) | 3-Me | — |
| Ph | Me | COtBu | A-101 (4-yl) | — | — |
| Ph | Me | COtBu | A-102 | — | — |
| Ph | Me | COtBu | A-103 (3-yl) | — | Me |
| Ph | Me | COtBu | A-104 (4-yl) | — | Me |
| Ph | Me | COtBu | A-105 | — | — |
| Ph | Me | COtBu | A-106 (3-yl) | — | — |
| Ph | Me | COtBu | A-107 | — | — |
| Ph | Me | COtBu | A-108 (3-yl) | — | — |
| Ph | Me | COtBu | A-109 | — | — |
| Ph | Me | COtBu | A-110 (4-yl) | 3-Me | — |
| Ph | Me | COtBu | A-111 | — | — |
| Ph | Me | COtBu | A-112 (4-yl) | 3-Me | — |
| Ph | Me | COtBu | A-113 | — | — |
| Ph | Me | COtBu | A-114 (3-yl) | — | — |
| Ph | Me | COtBu | A-115 | — | — |
| Ph | Me | COtBu | A-116 (3-yl) | — | — |
| Ph | Me | COtBu | A-117 (4-yl) | — | — |
| Ph | Me | COtBu | A-118 (4-yl) | — | — |
| Ph | Me | COtBu | A-119 | — | — |
| Ph | Me | COtBu | A-120 (4-yl) | — | Me |
| Ph | Me | COtBu | A-121 | — | — |
| Ph | Me | COtBu | A-122 (7-yl) | — | Me |
| Ph | Me | COtBu | A-123 (4-yl) | — | — |
| Ph | Me | COtBu | A-124 (8-yl) | — | — |
| Ph | Me | COtBu | A-125 (4-yl) | — | — |
| Ph | Me | COtBu | A-126 (8-yl) | — | — |
| Ph | Me | COtBu | A-127 (4-yl) | — | — |
| Ph | Me | COtBu | A-128 (8-yl) | — | — |
| Ph | Me | COtBu | A-129 (4-yl) | — | — |
| Ph | Me | COtBu | A-130 (8-yl) | — | — |
| Ph | Me | COtBu | A-131 (2-yl) | — | — |
| Ph | Me | COtBu | A-132 (8-yl) | — | — |
| Ph | Me | COtBu | A-133 | — | — |
| Ph | Me | COtBu | A-134 (8-yl) | — | — |
| Ph | Me | COtBu | A-135 (4-yl) | — | — |
| Ph | Me | COtBu | A-136 (8-yl) | — | — |
| Ph | Me | COtBu | A-137 (4-yl) | — | — |
| Ph | Me | COtBu | A-138 (8-yl) | — | — |
| Ph | Me | COtBu | A-139 (4-yl) | — | — |
| Ph | Me | COtBu | A-140 (8-yl) | — | — |
| Ph | Me | COtBu | A-141 (4-yl) | — | — |
| Ph | Me | COtBu | A-142 (8-yl) | — | — |
| Ph | Me | COtBu | A-143 (4-yl) | — | — |
| Ph | Me | COtBu | A-144 (6-yl) | — | — |
| Ph | Me | COtBu | A-145 | — | — |
| Ph | Me | COtBu | A-146 | — | Me |
| Ph | Me | COtBu | A-147 (2-yl) | — | Me |

TABLE 2-continued

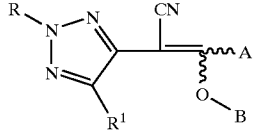

| R | R¹ | B | A | Y₁ | Y₃ |
|---|----|----|---|----|----|
| Ph | Me | COtBu | A-148 (7-yl) | — | — |
| Ph | Me | COtBu | A-149 (2-yl) | — | — |
| Ph | Me | COtBu | A-150 (7-yl) | — | — |
| Ph | Me | COtBu | A-151 (2-yl) | — | — |

Where the compounds of the present invention are used as pesticides, in general, they can be mixed with a suitable solid carrier or liquid carrier, optionally along with surfactant, penetrating agent, spreading agent, thickner, anti-freezing agent, binder, anti-caking agent, sliding agent, stabilizer, and the like, and can be formulated into any desired forms for practical use, such as soluble concentrates, emulsifiable concentrates, wettable powders, water soluble powders, water dispersible granules, water soluble granules, suspension concentrates, concentrated emulsions, suspoemulsions, microemulsions, dustable powders, granules and gels. From the viewpoint of an elimination or reduction of labor and an improvement of safety, the formulations in any desired forms described above may be included into a water soluble bag.

The solid carrier includes, for example, natural minerals such as quartz, kaolinite, pyrofilite, Celicite, talc, bentonite, acid clay, attapulgite, zeolite and diatomaceous earth, inorganic salts such as calcium carbonate, ammonium sulfate, sodium sulfate and potassium chloride, synthetic silicic acids and synthetic silicates.

The liquid carrier includes, for example, alcohols such as ethylene glycol, propylene glycol and isopropanol, aromatic hydrocarbons such as xylene, alkylbenzene and alkylnaphthalene, ethers such as butylcellosolb, ketones such as cyclohexanone, esters such as r-butyrolactone, amides such as N-methylpyrrolidone, N-octylpyrrolidone, vegetable oil such as soybean oil, rapeseed oil, cottonseed oil and castor oil, and water.

These solid and liquid carriers may be used alone, or in a mixture of two or more carriers.

The surfactants includes, for example, nonionic surfactants such as polyoxyethylene alkylether, polyoxyethylene alkylarylether, polyoxyethylene styrylphenylether, polyoxyethylene polyoxypropylene block copolymer, polyoxyethylene fatty ester, sorbitan fatty ester and polyoxyethylene sorbitan fatty ester; anionic surfactants such as alkyl sulfate, alkylbenzene sulfonate, lignin sulfonate, alkylsulfo succinate, naphthalene sulfonate, alkylnaphthalene sulfonate, a salt of condensate of naphthalene sulfonate with formalin, a salt of condensate of alkylnaphthalene sulfonate with formalin, polyoxyethylene alkylarylether sulfate and phosphate, polyoxyethylene styrylphenylether sulfate and phosphate, polycarboxylate and polystyrene sulfonate; cationic surfactants such as a salt of alkylamine and alkyl quaternary ammonium salt, and amphoteric surfactants such as amino acid type and betaine type.

The amount of the surfactant is not particularly limited, but in general, is 0.05 to 20 parts by weight based on 100 parts by weight of the formulation of the present invention. In addition, these surfactants may be used alone or in a mixture of two or more surfactants.

In case where the compounds of the present invention are used as agricultural chemicals, they can be combined with any other herbicides, various insecticides, acaricides, nematocides, fungicides, plant growth regulators, synergists, fertilizer and soil improvers, when they are formulated into preparations for practical use or while they are actually used through spraying or the like.

In particular, the combination of the compounds of the invention and other agricultural chemicals or plant hormones will be advantageous in that the amount of the chemicals to be used can be reduced thereby resulting in the reduction of the costs for the treatment, and that the mixed chemicals exhibit synergistic effects to broaden the insecticidal spectrum while displaying higher pesticidal activities. If desired, the compounds of the invention can be combined with a plurality of known agricultural chemicals. For the agricultural chemicals capable of being combined with the compounds of the invention, for example, the compounds described in Farm Chemicals Handbook, 1994 are referred. Concretely, the general names thereof are as follows, to which the present invention are not limited.

Fungicides: acibenzolar-S-methyl, acylaminobenzamide, amobam, ampropyfos, anilazine, azaconazole, azoxystrobin, benalaxyl, benodanil, benomyl, benthiazole, benzamacril, binapacryl, biphenyl, bitertanol, bethoxazine, bordeaux mixture, blasticidin-S, bromoconazole, bupirimate, buthiobate, calcium polysulfide, captafol, captan, copper oxychloride, carpropamid, carbendazim, carboxin, CGA-279202, chinomethionat, chlobenthiazone, chlorfenazol, chloroneb, chlorothalonil, chlozolinate, cufraneb, cymoxanil, cyproconazol, cyprodinil, cyprofuram, dazomet, debacarb, dichlorophen, diclobutrazol, dichlofluanid, dichlomedine, dicloran, diethofencarb, dichlocymet, difenoconazole, diflumetorim, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadone, fenarimol, febuconazole, fenamidone, fendazosulam, fenfuram, fenhexamid, fenpiclonil, fenpropidin, fenpropimorph, fentin, ferbam, ferimzone, fluazinam, fludioxonil, fluoroimide, fluquinconazole, flusilazole, flusulfamide, flutolanil, flutriafol, folpet, fosetyl-aluminium, fuberidazole, furalaxyl, furametpyr, guazatine, hexachlorobenzene, hexaconazole, hymexazol, imazalil, imibenconazole, iminoctadine, ipconazole, iprobenfos, iprodion, isoprothiolane, iprovalicarb, kasugamycin, kresoxim-methyl, mancopper, mancozeb, maneb, mepanipyrim, mepronil, metalaxyl, metconazole, methasulfocarb, metiram, metominostrobin, myclobutanil, MTF-753, nabam, nickel bis(dimethyldithiocarbamate), nitrothal-isopropyl, nuarimol, NNF-9425, octhilinone, ofurace, oxadixyl, oxycarboxin, oxopoconazole fumarate, pefurzoate, penconazole, pencycuron, phthalide, piperalin, polyoxins, potassium hydrogen carbonate, probenazole, prochloraz, procymidone, propamocarb hydrochloride, propiconazole, propineb, pyrazophos, pyrifenox, pyrimethanil, pyroquilon, quinomethionate, quinoxyfen, quintozene, RH7281, sodium hydrogen carbonate, sodium hypochlorite, sulfur, spiroxamine, tebuconazole, tecnazene, tetraconazole, thiabendazole, thiadiazin/milneb, thifluzamide, thiophanate-methyl, thiram, tolclofos-methyl, tolylfluanid, triadimefon, toriadimenol, triazoxide, tricyclazole, tridemorph, triflumizole, triforine, triticonazole, validamycin, vinclozolin, zinc sulfate, zineb, ziram and an extract from mycelium of shiitake (*Cortinellus shiitake*);

Bactriocides: strptomycin, tecloftalam, oxyterracycline and oxolinic acid;

Nematocides: aldoxycarb, cadusafos, fosthiazate, fosthietan, oxamyl and fenamiphos;

Acaricides: acequinocyl, amitraz, bifenazate, bromopropylate, chinomethionat, chlorobenzilate, clofentezine, cyhexatine, dicofol, dienochlor, etoxazole, fenazaquin, fenbutatin oxide, fenpropathrin, fenproximate, halfenprox, hexythiazox, milbemectin, propargite, pyridaben, pyrimidifen and tebufenpyrad;

Insecticides: abamectin, acephate, acetamipirid, aldicarb, allethrin, azinphos-methyl, bendiocarb, benfuracarb, bensultap, bifenthrin, buprofezin, butocarboxim, carbaryl, carbofuran, carbosulfan, cartap, chlorofenapyr, chlorpyrifos, chlorfenvinphos, chlorfluazuron, clothianidin, chromafenozide, chlorpyrifos-methyl, cycloprothrin, cyfluthrin, beta-cyfluthrin, cypermethrin, cyromazine, cyhalothrin, lamda-cyhalothrin, deltamethrin, diafenthiuron, diazinon, diacloden, diflubenzuron, dimethylvinphos, diofenolan, disulfoton, dimethoate, emamectin-benzoate, EPN, esfenvalerate, ethiofencarb, ethiprole, etofenprox, etrimfos, fenitrothion, fenobucarb, fenoxycarb, fenpropathrin, fenvalerate, fipronil, fluacrypyrim, flucythrinate, flufenoxuron, flufenprox, tau-fluvalinate, fonophos, formetanate, formothin, furathiocarb, halofenozide, hexaflumuron, hydramethyinon, imidacloprid, isofenphos, indoxacarb, isoprocarb, isoxathion, lufenuron, malathion, metaldehyde, methamidophos, methidathion, methacrifos, metalcarb, methomyl, methoprene, methoxychlor, methoxyfenozide, monocrotophos, muscalure, nidinotefuran, nitenpyram, omethoate, oxydemeton-methyl, oxamyl, parathion, parathion-methyl, permethrin, phenthoate, phoxim, phorate, phosalone, phosmet, phosphamidon, pirimicarb, pirimiphos-methyl, profenofos, protrifenbute, pymetrozine, pyraclofos, pyriproxyfen, rotenone, sulprofos, silafluofen, spinosad, sulfotep, tebfenozide, teflubenzuron, tefluthorin, terbufos, tetrachlorvinphos, thiacloprid, thiocyclam, thiodicarb, thiamethoxam, thiofanox, thiometon, tolfenpyrad, tralomethrin, trichlorfon, triazuron, triflumuron and vamidothion.

The dose of the compounds of the present invention varies depending on an applicaction place, an application time, an application method, cultivation crops, etc. In general, it may be between approximately 0.005 kg and 50 kg per hectare (ha) in terms of the amount of the active ingredient.

BEST MODE FOR CARRYING OUT THE INVENTION

Now, formulation examples comprising the compounds of the invention are mentioned below, to which the invention is not limited. In the following formulation examples, "part" or "parts" are by weight.

[Wettable Powders]

| | |
|---|---|
| Compound of the invention | 0.1 to 80 parts |
| Solid carrier | 5 to 98.9 parts |
| Surfactant | 1 to 10 parts |
| Others | 0 to 5 parts |

The others include, for example, anti-caking agent, stabilizer, etc.

[Emulsifiable Concentrates]

| | |
|---|---|
| Compound of the invention | 0.1 to 30 parts |
| Liquid carrier | 45 to 95 parts |
| Surfactant | 4.9 to 15 parts |
| Others | 0 to 10 parts |

The others include, for example, spreading agent, stabilizer, etc.

[Suspension Concentrates]

| | |
|---|---|
| Compound of the invention | 0.1 to 70 parts |
| Liquid carrier | 15 to 98.89 parts |
| Surfactant | 1 to 12 parts |
| Others | 0.01 to 30 parts |

The others include, for example, anti-freezing agent, thickener, etc.

[Water Dispersible Granules]

| | |
|---|---|
| Compound of the invention | 0.1 to 90 parts |
| Solid carrier | 0 to 98.9 parts |
| Surfactant | 1 to 20 parts |
| Others | 0 to 10 parts |

The others include, for example, binder, stabilizer, etc.

[Soluble Concentrates]

| | |
|---|---|
| Compound of the invention | 0.01 to 70 parts |
| Liquid carrier | 20 to 99.99 parts |
| Others | 0 to 10 parts |

The others include, for example, anti-freezing agent, spreading agent, etc.

[Granules]

| | |
|---|---|
| Compound of the invention | 0.01 to 80 parts |
| Solid carrier | 10 to 99.99 parts |
| Others | 0 to 10 parts |

The others include, for example, binder, stabilizer, etc.

[Dustable Powders]

| | |
|---|---|
| Compound of the invention | 0.01 to 30 parts |
| Solid carrier | 65 to 99.99 parts |
| Others | 0 to 5 parts |

The others include, for example, anti-drifting agent, stabilizer, etc.

FORMULATION EXAMPLES

Now, Formulation Examples of pesticides comprising the compounds of the present invention as an active ingredient are shown below, which, however, are not intended to restrict the scope of the present invention. In the following Formulation Examples, "part" or "parts" are by weight.

FORMULATION EXAMPLE 1

Wettable Powder

| | |
|---|---|
| Compound No. 17 of the invention | 20 parts |
| Pyrrofilite | 76 parts |
| Solpol 5039 | 2 parts |
| (trade name, a mixture of non-ionic surfactant and anionic surfactant, manufactured by Toho Chemical Co., Ltd.) | |
| Carplex #80D | 2 parts |
| (trade name, a synthetic silicic acid hydrate manufactured by Shionogi Pharmaceutical Co., Ltd.) | |

The above-mentioned components are homogeneously mixed and ground to form a wettable powder.

FORMULATION EXAMPLE 2

Emulsifiable Concentrate

| | |
|---|---|
| Compound No. 17 of the invention | 5 parts |
| Xylene | 75 parts |
| N-methylpyrolidone | 15 parts |
| Solpol 2680 | 5 parts |
| (trade name, a mixture of non-ionic surfactant and anionic surfactant, manufactured by Toho Chemical Co., Ltd.) | |

The above-mentioned components are homogeneously mixed to form an emulsifiable concentrate.

FORMULATION EXAMPLE 3

Suspension Concentrate (Flowable)

| | |
|---|---|
| Compound No. 17 of the invention | 25 parts |
| Agrisol S-710 | 10 parts |
| (trade name, non-ionic surfactant manufactured by Kao Corp.) | |
| Runox 1000C | 0.5 parts |
| (trade name, anionic surfactant manufactured by Toho Chemical Co., Ltd.) | |
| Xanthane gum | 0.2 parts |
| Water | 64.3 parts |

The above-mentioned components are homogeneously mixed and ground in wet to form a suspension concentrate.

FORMULATION EXAMPLE 4

Water Dispersible Granule (Dry Flowable)

| | |
|---|---|
| Compound No. 17 of the invention | 75 parts |
| Hitenol NE-15 | 5 parts |
| (trade name, anionic surfactant manufactured by Daiichi Industrial Pharmaceutical Co. Ltd.) | |
| Vanilex N | 10 parts |
| (trade name, anionic surfactant manufactured by Japan Paper-manufacturing Co., Ltd.) | |
| Carplex #80D | 10 parts |
| (trade name, a synthetic silicic acid hydrate manufactured by Shionogi Pharmaceutical Co., Ltd.) | |

The above-mentioned components are homogeneously mixed and ground, then mixed with stirring after adding a small amount of water, and are granulated with an extrusion granulator, and dried into a water dispersible granule.

FORMULATION EXAMPLE 5

Granule

| | |
|---|---|
| Compound No. 17 of the invention | 5 parts |
| Bentonite | 50 parts |
| Talc | 45 parts |

The above-mentioned components are homogeneously mixed and ground, then mixed with stirring after adding a small amount of water, and are granulated with an extrusion granulator, and dried into a granule.

FORMULATION EXAMPLE 6

Dustable Powder

| | |
|---|---|
| Compound No. 17 of the invention | 3 parts |
| Carplex #80D | 0.5 parts |
| (trade name, a synthetic silicic acid hydrate manufactured by Shionogi Pharmaceutical Co., Ltd.) | |
| Kaolinite | 95 parts |
| Diisopropyl phosphate | 1.5 parts |

The above-mentioned components are homogeneously mixed and ground to form a dustable powder.

Upon use, the wettable powder, emulsifiable concentrate, flowable and water dispersible granule are diluted from 50 to 20000 times with water, and applied in amount of from 0.005 to 50 kg/ha in terms of the active ingredient.

Now, Synthesis Examples and Test Examples of the compounds of the present invention are shown as Examples below, which, however, are not intended to restrict the scope of the invention.

REFERENCE EXAMPLE 1

Synthesis of Cyanomethyltriazole Derivative (A Method)

A synthesis method of cyanomethyltriazole according to A method described above will be explained below. Novel compounds also are included in intermediates described below. In the physical properties indicated below, the unit of melting points is ° C. and the values of NMR are chemical shifts in 1H-NMR(CDCl$_3$, ppm).

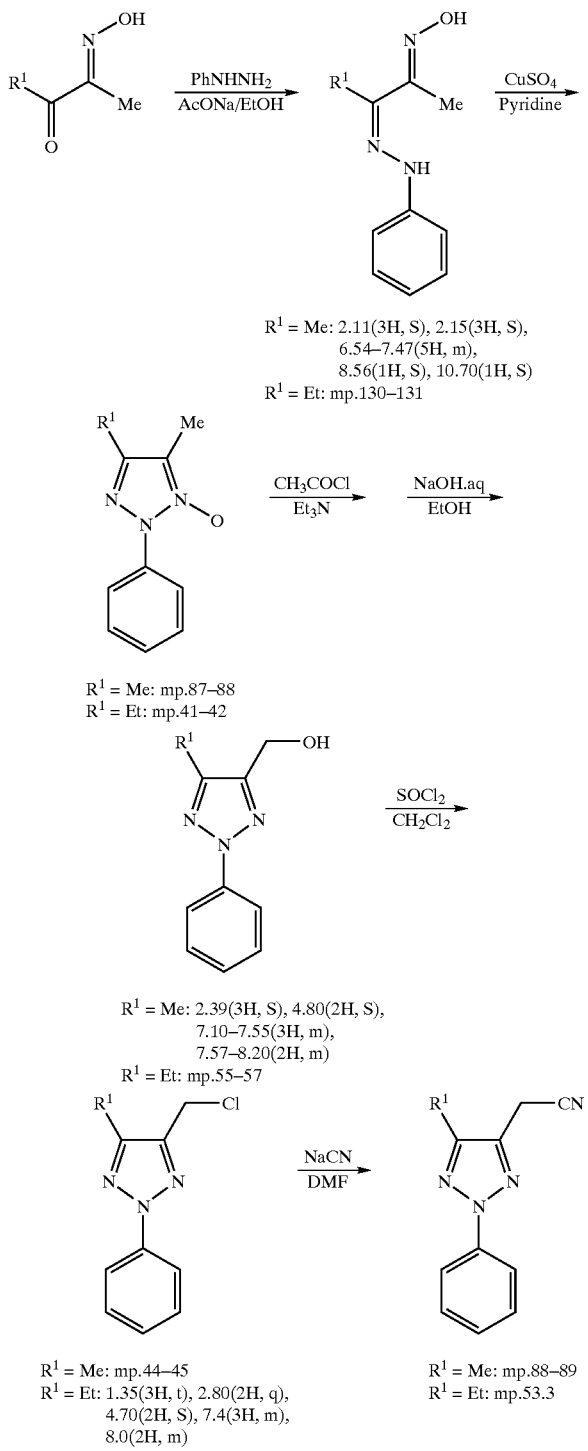

1) Synthesis of (1-aza-3-(Hydroxyimino)-2-methylbut-1-enyl)phenylamine 10 g of phenylhydrazine hydrochloride was dissolved in 100 ml of ethanol, and 6.8 g of sodium acetate was added thereto under cooling with ice. 7.0 g of diacetyl monoxime was added dropwise to the reaction solution, then stirred for 1 hour at room temperature. After ethanol was distilled off, the residue was washed with water to obtain 12.0 g of the aimed compound.

2) Synthesis of 4,5-Dimethyl-2-phenyl-1,2,3-triazol-1-oxide 15.0 g of copper(II) sulfate (penta hydrate) dissolved in 60 ml of water added dropwise to 11.5 g of (1-aza-3-(hydroxyimino)-2-methylbut-1-enyl)phenylamine dissolved in 120 ml of pyridine at room temperature. After stirring overnight at room temperature, concentrated hydrochloric acid was added to the stirred solution under cooling with ice to make it acid, then extracted with chloroform. The organic phase was washed with water and a saturated salt solution, then dried over anhydrous sodium sulfate. After the solvent was distilled off, the deposited crystals was washed with isopropyl ether to obtain 8.8 g of the aimed compound.

3) Synthesis of (5-Methyl-2-phenyl-1,2,3-triazol-4-yl)methan-1-ol 7.1 g of 4,5-dimethyl-2-phenyl-1,2,3-triazol-1-oxide was dissolved in 25 ml of toluene, and heated to 80° C. 4.8 g of acetyl chloride diluted with 13 ml of toluene and 9.1 ml of triethylamine diluted with 13 ml of toluene were simultaneouly added dropwise thereto, keeping the temperature below 85° C. After stirring for 1 hour at 80° C., 2.5 ml of acetyl chloride diluted with 5 ml of toluene and 4.5 ml of triethylamine diluted with 5 ml of toluene were simultaneously added. After stirring for 1 hour at 80° C., the solution was left overnight at room temperature. 7 ml of 30% aqueous solution of sodium hydroxide was added, then toluene and triethylamine were distilled off under reduced pressure. 5 ml of ethanol and 30% aqueous solution of sodium hydroxide were added, and refluxed with heating for 1 hour. After ethanol was distilled off under reduced pressure, 50 ml of 10% saline solution was added, and left for some time at room temperature. The deposited crystals was dissolved in ethyl acetate, washed with water and a saturated salt solution, then dried over anhydrous sodium sulfate. After the solvent was distilled off, the residue was purified through silica gel column chromatography (hexan/ethyl acetate=1/2), then washed with hexan/diisopropyl ether (=10/1) to obtain 5.7 g of the aimed compound.

4) Synthesis of 4-Chloromethyl-5-methyl-2-phenyl-1,2,3-triazol 5.0 g of (5-methyl-2-phenyl-1,2,3-triazol4-yl)methan-1-ol was dissolved in 35 ml of dichloromethane, then 6.3 g of thionyl chloride was added dropwise thereto under cooling with ice. After stirring for 1 hour at room temperature, 100 ml of water was added. The resulting solution was made alkaline with 8 g of potassium carbonate, then extracted with chloroform. The organic phase was washed with water and a saturated salt solution, then dried over anhydrous sodium sulfate. After the solvent was distilled off, 5.2 g of the aimed compound was obtained.

5) Synthesis of 2-(5-Methyl-2-phenyl-1,2,3-triazol4-yl)ethanenitrile 1.8 g of sodium cyanide was suspended in 30 ml of DMF, and 5.0 g of 4-chloromethyl-5-methyl-2-phenyl-1,2,3-triazol was added under cooling with ice. After stirring for 3 hours at room temperature, an aqueous solution of sodium hydroxide was added to the reaction solution to make it alkaline, and extracted with toluene. The organic phase was washed with water and a saturated salt solution, then dried over anhydrous sodium sulfate. After the solvent was distilled off, the deposited crystals were washed with hexane to obtain 4.3 g of the aimed compound.

2-(5-ethyl-2-phenyl-1,2,3-triazol4-yl)ethanenitrile was synthesized in a similar manner of 1) to 5) described above except that 2-(hydroxyimino)pentane-3-on was used as a starting material.

REFERENCE EXAMPLE 2

Synthesis of Cyanomethyltriazole Derivative (B Method)

A synthesis method of cyanomethyltriazole according to B method described above will be explained below. Novel compounds also are included in intermediates described below. In the physical properties indicated below, the units of melting points are ° C. and the values of NMR are chemical shifts in 1H-NMR(CDCl₃, ppm).

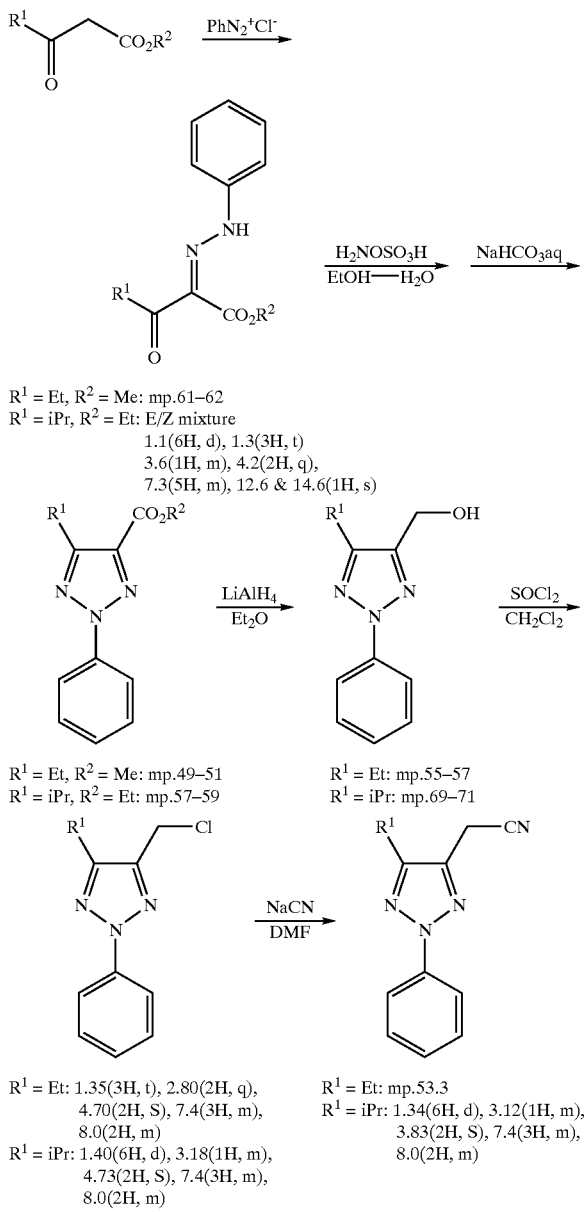

R¹ = Et, R² = Me: mp.61–62
R¹ = iPr, R² = Et: E/Z mixture
1.1(6H, d), 1.3(3H, t)
3.6(1H, m), 4.2(2H, q),
7.3(5H, m), 12.6 & 14.6(1H, s)

R¹ = Et, R² = Me: mp.49–51
R¹ = iPr, R² = Et: mp.57–59

R¹ = Et: mp.55–57
R¹ = iPr: mp.69–71

R¹ = Et: 1.35(3H, t), 2.80(2H, q), 4.70(2H, S), 7.4(3H, m), 8.0(2H, m)
R¹ = iPr: 1.40(6H, d), 3.18(1H, m), 4.73(2H, S), 7.4(3H, m), 8.0(2H, m)

R¹ = Et: mp.53.3
R¹ = iPr: 1.34(6H, d), 3.12(1H, m), 3.83(2H, S), 7.4(3H, m), 8.0(2H, m)

1) Synthesis of Methyl-3-aza-3-(phenylamino)-2-propanoylprop-2-enoate 8.83 g of sodium nitrite dissolved in 25 ml of water was added dropwise to 11.67 g of aniline dissolved in 130 ml of 2N hydrochloric acid at 0° C. 32.8 g of sodium acetate and the reaction solution comprising diazonium salt were simultaneously added to 16.25 g of methylpropionyl acetate suspended in 100 ml of water at 21–23° C. The deposited solid was filtrated out, and washed with water to obtain the aimed compound.

2) Synthesis of Ethyl-5-ethyl-2-phenyl-1,2,3-triazole-4-carboxylate

Hydroxylamine-O-sulfonic acid dissolved in 200 ml of water was added dropwise at room temperature to methyl-3-aza-3-(phenylamino)-2-propanoylprop-2-enoate synthesized in 1) dissolved in 300 ml of ethanol. After stirring overnight at room temperature, the reaction solution was neutralized with sodium hydrogencarbonate, and stirred for 3 hours at room temperature. Ethanol was distilled off under reduced pressure, and extracted with ethyl acetate. The organic phase was washed with water, and dried over anhydrous sodium sulfate. After the solvent was distilled off, the residue was purified through silica gel column chromatography (chloroform) to obtain 13.9 g of the aimed compound.

3) Synthesis of (5-Ethyl-2-phenyl-1,2,3-triazol-4-yl)methan-1-ol 11.55 g of ethyl-5-ethyl-2-phenyl-1,2,3-triazole-4-carboxylate dissolved in a mixed solvent of 150 ml of ether and 30 ml of THF was added dropwise at 3–8° C. to LiAlH₄ suspended in 100 ml of ether. After stirring overnight at room temperature, a small amount of saturated sodium sulfate solution was added thereto. Insoluble materials were filtered off, and the filtrate was dried over anhydrous sodium sulfate. The solvent was distilled off to obtain 9.40 g of the aimed compound.

(5-isopropyl-2-phenyl-1,2,3-triazol-4-yl)methan-1-ol was synthesized in a similar manner of 1) to 3) described above except that ethylisobutyryl acetate was used as a starting material.

Next, cyanomethyltriazole derivatives can be synthesized similarly to Reference Example 1.

SYNTHESIS EXAMPLE 1

Synthesis of 3-(2,4-Dimethylthiazol-5-yl)-3-hydroxy-2-(5-methyl-2-phenyl-1,2,3-triazol4-yl)acrylonitrile (Compound No. 20)

0.90 g of 4-cyanomethyl-5-methyl-2-phenyl-1,2,3-triazole and 1.04 g of 1-(2,4-dimethylthiazol-5-carbonyl)pyrazole were dissolved in tetrahydrofuran, and 1.02 g of potassium tert-butoxide was added thereto at 0° C. After stirring for 1 hour at room temperature, diluted hydrochloric acid was added to the reaction solution to make it acid. The solution was extracted with ethyl acetate, and dried over anhydrous sodium sulfate. The solvent was distilled off under reduced pressure, and the resulting solid was washed with isopropyl ether to obtain 0.79 g of the aimed compound. m.p.: 117–118° C.

SYNTHESIS EXAMPLE 2

Synthesis of 3-(2,4-Dimethylthiazol-5-yl)-3-2-(5-methyl-2-phenyl-1,2,3-triazol-4-yl)acrylonitrile (Compound No. 20)

0.6 g of 3-(2,4-dimethylthiazol-5-yl)-3-hydroxy-2-(5-methyl-2-phenyl-1,2,3-triazol-4-yl)acrylonitrile was dissolved in chloroform, 0.22 g of triethylamine was added thereto, and 0.26 g of pivaloyl chloride was further added dropwise. After stirring for 3 hours at room temperature, the solution was washed with water, dried over anhydrous sodium sulfate, and the solvent was distilled off under reduced pressure. The resulting crystals were washed with a mixed solvent of hexane/isopropyl ether to obtain 0.59 g of the aimed compound (a mixture of E-form and Z-form). m.p.: 119–122° C.

In accordance with the above-mentioned reaction schemes or Synthesis Examples, various compounds of the present invention were produced, of which the structure and the melting point are shown in Table 3 below. Unless otherwise specifically indicated, the compounds shown in the table are in form of a mixture of E-form and Z-form. The abbreviations in the table have the same meanings as those mentioned above.

TABLE 3

| No. | R | R¹ | B | A | Y₁ | Y₂ | Y₃ | m.p. (° C.), ratio of isomers |
|---|---|---|---|---|---|---|---|---|
| 1 | 2-Cl—Ph | Me | COtBu | A-3 | Me | Me | — | 109.5–110, E-form or Z-form |
| 2 | 2-Cl—Ph | Me | COtBu | A-3 | Me | Me | — | resinous, Z-form or E-form |
| 3 | Ph | Me | H | A-1 | Me | Me | Me | resinous |
| 4 | Ph | Me | COtBu | A-1 | Me | Me | Me | 139–142, E-form or Z-form |
| 5 | Ph | Me | COtBu | A-1 | Me | Me | Me | 133–135, Z-form or E-form |
| 6 | Ph | Me | H | A-1 | Cl | Me | Me | 140–141 |
| 7 | Ph | Me | COtBu | A-1 | Cl | Me | Me | 137–138, E-form or Z-form |
| 8 | Ph | Me | H | A-1 | H | Me | Me | 118–119 |
| 9 | Ph | Me | COtBu | A-1 | H | Me | Me | 104–108, E-form/Z-form mixture |
| 10 | Ph | Me | H | A-1 | Me | H | Me | 140–141 |
| 11 | Ph | Me | COtBu | A-1 | Me | H | Me | 171–177, E-form/Z-form mixture |
| 12 | Ph | Me | H | A-1 | Me | Br | Me | 171–177 |
| 13 | Ph | Me | COtBu | A-1 | Me | Br | Me | 163–164, E-form or Z-form |
| 14 | 2-Me—Ph | Me | H | A-1 | Me | Me | Me | resinous |
| 15 | 2-Me—Ph | Me | COtBu | A-1 | Me | Me | Me | resinous, E-form/Z-form mixture |
| 16 | 2-F—Ph | Me | H | A-1 | Me | Me | Me | 126–127 |
| 17 | 2-F—Ph | Me | COtBu | A-1 | Me | Me | Me | 113–116, 3/2 |
| 18 | 2,6-Cl₂—Ph | Me | H | A-1 | Me | Me | Me | 203–204 |
| 19 | 2,6-Cl₂—Ph | Me | COtBu | A-1 | Me | Me | Me | resinous, E-form/Z-form mixture |
| 20 | Ph | Me | H | A-3 | Me | Me | — | 117–118 |
| 21 | Ph | Me | COtBu | A-3 | Me | Me | — | 119–122, E-form/Z-form mixture |
| 22 | Ph | Me | H | A-3 | CF₃ | Me | — | 143–145 |
| 23 | Ph | Me | COtBu | A-3 | CF₃ | Me | — | 141–142, E-form or Z-form |
| 24 | Ph | Me | COPh | A-3 | CF₃ | Me | — | 115–118, E-form/Z-form mixture |
| 25 | Ph | CN | COtBu | A-1 | Me | Me | Me | resinous, 5/4 |
| 26 | Ph | Me | SO₂Me | A-1 | Me | Me | Me | resinous, 5/4 |
| 27 | Ph | Me | SO₂Ph | A-1 | Me | Me | Me | resinous, 4/1 |
| 28 | Ph | Me | CO(2-Cl—Ph) | A-1 | Me | Me | Me | resinous, 5/3 |
| 29 | Ph | Me | CO₂iBu | A-1 | Me | Me | Me | resinous, 2/1 |
| 30 | Ph | Me | CH₂OEt | A-1 | Me | Me | Me | resinous, 3/1 |
| 31 | Ph | Me | Me | A-1 | Me | Me | Me | resinous, 3/1 |
| 32 | 2-Cl—Ph | Me | H | A-1 | Me | Me | Me | resinous |
| 33 | 2-Cl—Ph | Me | COtBu | A-1 | Me | Me | Me | resinous, 2/3 |
| 34 | 2-Br—Ph | Me | H | A-1 | Me | Me | Me | resinous |
| 35 | 2-Br—Ph | Me | COtBu | A-1 | Me | Me | Me | resinous, 9/11 |
| 36 | tBu | Me | H | A-1 | Me | Me | Me | resinous |
| 37 | tBu | Me | COtBu | A-1 | Me | Me | Me | resinous, E-form/Z-form mixture |
| 38 | Ph | COOMe | H | A-1 | Me | Me | Me | resinous |
| 39 | Ph | CONMe₂ | COtBu | A-1 | Me | Me | Me | resinous, 4/1 |
| 40 | Ph | CO(N-piperidyl) | COtBu | A-1 | Me | Me | Me | resinous, 6/1 |
| 41 | 2-Me—Ph | Me | COtBu | A-1 | Cl | Me | Me | resinous, 1/1 |
| 42 | Ph | CH₂SMe | H | A-1 | Cl | Me | Me | 104–106 |
| 43 | Ph | CH₂SMe | COtBu | A-1 | Cl | Me | Me | resinous |
| 44 | Ph | nBu | H | A-1 | Cl | Me | Me | 121–123 |
| 45 | Ph | nBu | COtBu | A-1 | Cl | Me | Me | resinous, 1/1 |
| 46 | Ph | Et | H | A-1 | Cl | Me | Me | 125–127 |
| 47 | Ph | Et | COtBu | A-1 | Cl | Me | Me | resinous, 1/1 |
| 48 | Ph | nPr | H | A-1 | Cl | Me | Me | 91–93 |
| 49 | Ph | nPr | COtBu | A-1 | Cl | Me | Me | resinous, 1/1 |
| 50 | Ph | iPr | H | A-1 | Cl | Me | Me | 132–133 |
| 51 | Ph | iPr | COtBu | A-1 | Cl | Me | Me | resinous, 1/1 |
| 52 | Ph | CH₂OMe | COtBu | A-1 | Cl | Me | Me | 36.4–42.3, 2/1 |
| 53 | Ph | Me | Me | A-1 | Cl | Me | Me | 123.1–125.1, E-form |
| 54 | Ph | Me | CH₂OEt | A-1 | Cl | Me | Me | resinous, 1/1 |
| 55 | Ph | Me | SO₂Ph | A-1 | Cl | Me | Me | 140.1–141.7, E-form |
| 56 | Ph | Me | CO₂iBu | A-1 | Cl | Me | Me | resinous, 3/2 |
| 57 | Ph | Me | CO(2-Cl—Ph) | A-1 | Cl | Me | Me | 123.6–131.9, 4/3 |
| 58 | Ph | Me | SO₂Me | A-1 | Cl | Me | Me | resinous, 1/1 |
| 59 | Ph | Me | CO(2-pyridyl) | A-1 | Cl | Me | Me | 178.2–180.9, E-form or Z-form |
| 60 | Ph | Me | CO(2-pyridyl) | A-1 | Cl | Me | Me | resinous, Z-form or E-form |
| 61 | 2-MeO—Ph | Me | H | A-1 | Cl | Me | Me | 128–130 |
| 62 | 2-MeO—Ph | Me | COtBu | A-1 | Cl | Me | Me | resinous, 3/2 |
| 63 | 2-MeO—Ph | Me | H | A-1 | Me | Me | Me | 100–111 |
| 64 | 2-MeO—Ph | Me | COtBu | A-1 | Me | Me | Me | 135–137, E-form or Z-form |

TABLE 3-continued

| No. | R | R¹ | B | A | $Y_1$ | $Y_2$ | $Y_3$ | m.p. (° C.), ratio of isomers |
|---|---|---|---|---|---|---|---|---|
| 65 | 2-MeO—Ph | Me | COtBu | A-1 | Me | Me | Me | resinous, Z-form or E-form |
| 66 | Ph | nHex | H | A-1 | Cl | Me | Me | 109–110 |
| 67 | Ph | nHex | COtBu | A-1 | Cl | Me | Me | resinous |
| 68 | Ph | Me | COtBu | A-1 | Cl | Me | Me | 96–96.5, Z-form or E-form |
| 69 | 1-naphthyl | Me | H | A-1 | Cl | Me | Me | resinous |
| 70 | 1-naphthyl | Me | COtBu | A-1 | Cl | Me | Me | resinous, 3/7 |
| 71 | 2-Ph—Ph | Me | H | A-1 | Cl | Me | Me | resinous |
| 72 | 2-Ph—Ph | Me | COtBu | A-1 | Cl | Me | Me | resinous, E-form/Z-form mixture |
| 73 | 2-CF₃—Ph | Me | H | A-1 | Cl | Me | Me | resinous |
| 74 | 2-CF₃—Ph | Me | COtBu | A-1 | Cl | Me | Me | resinous, E-form/Z-form mixture |
| 75 | 2,6-F₂—Ph | Me | H | A-1 | Cl | Me | Me | resinous |
| 76 | 2,6-F₂—Ph | Me | COtBu | A-1 | Cl | Me | Me | resinous, 5/4 |
| 77 | Ph | H | COtBu | A-1 | Cl | Me | Me | 119–120, E-form or Z-form |
| 78 | tBu | H | COtBu | A-1 | Cl | Me | Me | resinous |
| 79 | tBu | Me | COtBu | A-3 | Me | Me | — | resinous, Z-form or E-form |
| 80 | tBu | Me | COtBu | A-3 | Me | Me | — | 111–113, E-form or Z-form |
| 81 | Ph | Me | COtBu | A-2 | Me | H | Me | 128–137, E-form/Z-form mixture |
| 82 | Ph | Me | COtBu | A-3 | Me | Me | — | 143–144, E-form or Z-form |
| 83 | Ph | Me | COtBu | A-3 | Me | Me | — | 136–138.5 |
| 84 | Ph | H | COtBu | A-3 | Me | Me | — | 104–105, Z-form or E-form |
| 85 | 2-Cl—Ph | Me | H | A-1 | Cl | Et | Me | resinous |
| 86 | 2-Cl—Ph | Me | COtBu | A-1 | Cl | Et | Me | resinous, 1/1 |
| 87 | Ph | iPr | H | A-1 | Me | Me | Me | resinous |
| 88 | Ph | nPr | H | A-1 | Me | Me | Me | resinous |
| 89 | Ph | iPr | COtBu | A-1 | Me | Me | Me | 125–125.5, Z-form<br>139–140, E-form |
| 90 | Ph | nPr | COtBu | A-1 | Me | Me | Me | resinous, 1/2 |
| 91 | Ph | nBu | COtBu | A-1 | Me | Me | Me | resinous, 1/1 |
| 92 | Ph | nBu | COtBu | A-3 | Me | Me | — | resinous, 1/1 |
| 93 | Ph | Et | COtBu | A-3 | Me | Me | — | resinous, 1/1 |
| 94 | Ph | Et | COtBu | A-1 | Me | Me | Me | 139–140, Z-form<br>119, E-form |
| 95 | Ph | nBu | H | A-1 | Me | Me | Me | resinous |
| 96 | Ph | nBu | H | A-3 | Me | Me | — | 111–113 |
| 97 | 2-Me—Ph | Me | COtBu | A-3 | Me | Me | — | resinous |
| 98 | 2-Me—Ph | Me | COCH₂Ph | A-3 | Me | Me | — | resinous |
| 99 | Ph | nBu | COCH₂Ph | A-1 | Me | Me | Me | resinous, 1/2 |
| 100 | Ph | cHex | H | A-3 | Me | Me | — | 104–106 |
| 101 | Ph | cHex | COtBu | A-3 | Me | Me | — | 128–130, E-form or Z-form |
| 102 | Ph | cHex | H | A-1 | Me | Me | Me | resinous |
| 103 | Ph | cHex | COtBu | A-1 | Me | Me | Me | resinous, 1/1 |
| 104 | Ph | Ph | H | A-1 | Me | Me | Me | resinous |
| 105 | Ph | Ph | COtBu | A-1 | Me | Me | Me | resinous, 1/1 |
| 106 | Ph | H | H | A-1 | Cl | Me | Me | 146–147 |
| 107 | Ph | Et | H | A-1 | Me | Me | Me | 112–115 |
| 108 | Ph | CH₂OEt | H | A-1 | Me | Me | Me | resinous |
| 109 | Ph | CH₂OEt | COtBu | A-1 | Me | Me | Me | 52.1–55.3 |
| 110 | Ph | CH₂OnBu | H | A-1 | Me | Me | Me | resinous |
| 111 | Ph | CH₂OnBu | COtBu | A-1 | Me | Me | Me | resinous, 1/1 |
| 112 | Ph | iPr | CO(3-pyridyl) | A-1 | Cl | Me | Me | resinous |
| 113 | Ph | iPr | CO₂Et | A-1 | Cl | Me | Me | resinous, 2/1 |
| 114 | Ph | iPr | CH₂OMe | A-1 | Cl | Me | Me | resinous, 2/1 |
| 115 | Ph | CH₂(N-morpholinyl) | H | A-1 | Me | Me | Me | 142.3–145.9 |
| 116 | Ph | CH₂(N-morpholinyl) | COtBu | A-1 | Me | Me | Me | resinous, 4/1 |
| 117 | Ph | Et | H | A-6 | F | H | — | 144.5–145.5 |
| 118 | Ph | Et | COtBu | A-6 | F | H | — | resinous, 1/1 |
| 119 | Ph | Et | H | A-6 | F | F | — | 165.5–166.5 |
| 120 | Ph | Et | COtBu | A-6 | F | F | — | resinous, 2/1 |
| 121 | Ph | CH₂OCH₂—CH₂OMe | H | A-1 | Me | Me | Me | resinous |
| 122 | Ph | CH₂OCH₂—CH₂OMe | COtBu | A-1 | Me | Me | Me | resinous |
| 123 | 2-pyridyl | Me | COtBu | A-1 | Me | Me | Me | resinous, E-form or Z-form |
| 124 | 2-pyridyl | Me | COtBu | A-1 | Me | Me | Me | 134–135, Z-form or E-form |
| 125 | 2-pyridyl | Me | H | A-1 | Me | Me | Me | 341 (decomp.) |

TABLE 3-continued

| No. | R | $R^1$ | B | A | $Y_1$ | $Y_2$ | $Y_3$ | m.p. (° C.), ratio of isomers |
|---|---|---|---|---|---|---|---|---|
| 126 | 2-pyridyl | Me | H | A-6 | F | F | — | 346.1 |
| 127 | 2-pyridyl | Me | COtBu | A-6 | F | F | — | 111–112 |
| 128 | Ph | $CH_2$(N-pyrazolyl) | H | A-1 | Me | Me | Me | 182.6–185.1 |
| 129 | Ph | $CH_2$(N-pyrazolyl) | COtBu | A-1 | Me | Me | Me | 133.3–135.8, 9/1 |
| 130 | Ph | $CH_2$(N-pyrazolyl) | COtBu | A-1 | Me | Me | Me | resinous, 1/4 |
| 131 | Ph | Et | CO(A-1) | A-1 | Me | Me | Me | 145–145.5 |
| 132 | Ph | iPr | H | A-3 | Me | Me | — | 90.1–92.5 |
| 133 | Ph | iPr | H | A-3 | $CF_3$ | Me | — | 106.3–108.9 |
| 134 | Ph | iPr | COtBu | A-3 | Me | Me | — | resinous, 1/1 |
| 135 | Ph | iPr | COtBu | A-3 | $CF_3$ | Me | — | resinous, 2/1 |
| 136 | Ph | Et | COtBu | A-1 | CN | Me | Me | resinous |
| 137 | Ph | Et | H | A-1 | CN | Me | Me | 129–130 |
| 138 | Ph | Et | H | A-7 | Cl | H | Me | 112–114 |
| 139 | Ph | Et | COtBu | A-7 | Cl | H | Me | resinous, 5/4 |

[Test Example]

Now, the following Test Examples are to demonstrate the usefulness of the compounds of the present invention as pesticides.

[Test Example 1] Acaricidal Test For Two-spotted Spider Mites (*Tetranychus urticae*)

The leaves of kidney bean plants were punched into 3.0 cm-diameter discs, using a leaf punch, and put onto moistured filter paper in a 7 cm-diameter styrol cup. Ten larvae of two-spotted spider mites (*Tetranychus urticae*) were put to each leaf. A 5% emulsion (or 25% wettable powder) of a compound of the invention was diluted with water containing a spreading agent to give a 500 ppm solution of the compound. The solution was sprayed over each cup in an amount of 2 ml/cup, using a rotary sprinkler, and the cups were stored in a thermostatic chamber at 25° C. After 96 hours passed, the mites in each cup were observed, and mortality of the mites was determined according to the following equation. Each compound was tested in that manner for two groups of dishes.

Mortality (%)=[number of insect killed/(number of insect killed+ number of living insect)]×100

In this test, the following compounds exhibited mortality of 80% or more: Compounds of the invention: Nos. 1–24, 26–30, 32–38, 40–52, 54–60, 62, 65–80, 82–124 and 127–136.

TEST EXAMPLE 2

Residual Effect Test for Citrus Red Mite (*Panonychus citri*)

A 5% emulsion (or 25% wettable powder) of a compound of the invention was diluted with water containing a spread-ing agent to give a solution of the compound with prescribed concentration. The solution was sprayed over each orange planted in a pot in an amount of 250 ml/pot, using a rotary sprinkler, and the pot were left in the open air. After the prescribed days, the leaves of orange plants were punched into 3.0 cm-diameter discs, using a leaf punch, and put onto moistured filter paper in a 7 cm-diameter styrol cup. Ten larvae of citrus red mite (*Panonychus citri*) were put to each leaf. Then, the cups were stored in a thermostatic chamber at 25° C. After 48 hours passed, the mites in each cup were observed, and mortality of the mites was determined according to the same equation as in Test Example 1. Each compound was tested in that manner for four groups of dishes. The results are shown in Tables 4–7 below.

In the test, the following Compound A described in WO97/40009 was used as a comparative compound.

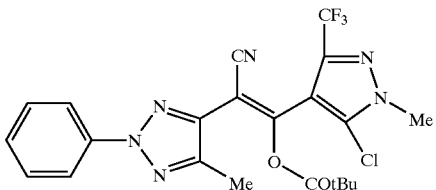

In the test, the following Compound A described in WO97/40009 was used as a comparative compound.

TABLE 4

| Compound No. | Concentration of spray solution (ppm) | Mortality (%) Days left in the open air after spraying the solution to orange planted in a pot ||||||||||
|---|---|---|---|---|---|---|---|---|---|---|---|
| | | 2 | 4 | 7 | 9 | 11 | 13 | 17 | 19 | 22 | 26 | 29 |
| 4 | 100 | 100 | 100 | 100 | 100 | 100 | 100 | 100 | 100 | 100 | 100 | 92.5 |
| 5 | 100 | 100 | 100 | 100 | 100 | 100 | 100 | 100 | 100 | 100 | 100 | 100 |
| 7 | 100 | 100 | 100 | 100 | 100 | 90.0 | 47.5 | 57.5 | — | — | — | — |
| 9 | 100 | 100 | 100 | 100 | 100 | 97.5 | 32.5 | — | — | — | — | — |
| 21 | 100 | 100 | 100 | 100 | 100 | 100 | 100 | 95.0 | 100 | 60.0 | 100 | 67.5 |
| A | 100 | 17.5 | 40.0 | — | — | — | — | — | — | — | — | — |

TABLE 5

| Compound No. | Concentration of spray solution (ppm) | Mortality (%) Days left in the open air after spraying the solution to orange planted in a pot |||||||
|---|---|---|---|---|---|---|---|---|
| | | 2 | 4 | 6 | 10 | 14 | 16 | 18 | 22 |
| 33 | 100 | 100 | 100 | 100 | 100 | 100 | 97.5 | 100 | 87.5 |
| 35 | 100 | 100 | 100 | 100 | 100 | 100 | 95.0 | 82.5 | 67.5 |
| A | 100 | 17.5 | 40.0 | — | — | — | — | — | — |

TABLE 6

| Compound No. | Concentration of spray solution (ppm) | Mortality (%) Days left in the open air after spraying the solution to orange planted in a pot |||||||
|---|---|---|---|---|---|---|---|---|
| | | 2 | 4 | 5 | 8 | 12 | 14 | 16 | 20 |
| 41 | 100 | 100 | — | 100 | 100 | 100 | 95.0 | 97.5 | 52.5 |
| 76 | 100 | 100 | — | 77.5 | 52.5 | — | — | — | — |
| A | 100 | 17.5 | 40.0 | — | — | — | — | — | — |

TABLE 7

| Compound No. | Concentration of spray solution (ppm) | Mortality (%) Days left in the open air after spraying the solution to orange planted in a pot ||||||
|---|---|---|---|---|---|---|---|---|
| | | 2 | 4 | 5 | 7 | 9 | 13 | 15 |
| 89[*1] | 100 | 100 | 92.5 | 100 | 100 | 100 | 100 | 52.5 |
| 90 | 50 | 100 | 100 | 100 | 100 | 100 | 65.0 | 27.5 |
| 91 | 100 | 100 | 100 | 100 | 100 | 100 | 100 | 37.5 |
| 92 | 50 | 100 | 97.5 | 100 | 92.5 | 92.5 | 45.0 | — |
| 93 | 100 | 100 | 100 | 100 | 100 | 100 | 50.0 | 40.0 |
| 94[*2] | 50 | 100 | 100 | 100 | 100 | 100 | 90.0 | 52.5 |
| A | 100 | 17.5 | 40.0 | — | — | — | — | — |

[*1] A mixture of an equal amount of Z-form and E-form
[*2] Z-form

Industry Applicability

The present invention provides novel insecticides and acaricides having long-term residual effect.

What is claimed is:

1. Acrylonitrile compounds of formula (1):

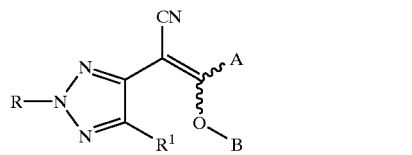

wherein,

R of a $C_1$–$C_6$ alkyl, a $C_3$–$C_7$ cycloalkyl optionally substituted by a $C_1$–$C_4$ alkyl, a phenyl optionally substituted by X, a naphthyl or a pyridyl, $R^1$ is H, a halogen, a $C_1$–$C_6$ alkyl, a $C_3$–$C_7$ cycloalkyl optionally substituted by a $C_1$–$C_6$ alkoxy, a $C_1$–$C_4$ haloalkyl, a $C_2$–$C_6$ alkoxyalkyl, $CH_3OC_2H_4OCH_2$, a $C_2$–$C_6$ alkylsulfenylalkyl, a $C_2$–$C_6$ alkylsulfinyalkyl, a $C_2$–$C_6$ alkylsulonylalkyl, a $C_1$–$C_3$alkyl substituted by phenyl, a phenyl, $C_7$–$C_{10}$ phenoxyalkyl, COORa, CONHRb, CONRaRb, CORa, CO(piprridyl), CN, $NO_2$ or $CH_2J$, A is

A-3

B is H, a $C_1$–$C_4$ alkyl, a $C_2$–$C_4$ alkoxyalkyl, $CH_2SCH_3$, $CH_2OC_2H_4OCH_3$, a $C_1$–$C_4$ alkyl substituted by Rc or Rd, a tetrahydropyranyl, $Si(CH_3)_3$, $SO_2Re$, $SO_2NHRb$, $SO_2NRaRb$, C(S)NHRb, C(S)NRaRb, $CH_2COORa$, C(O)Rf, P(O)RgRh, P(S)RgRh, an alkali metal, an alkaline earth metal or NHRiRjRk, X is one to three substitutes as freely selected from a halogen, a $C_1$–$C_4$alkyl, a $C_1$–$C_4$ haloalkyl, a $C_1$–$C_4$ alkoxy, a $C_1$–$C_4$ alkylsulfenyl, a $C_1$–$C_4$ alkylsulfinyl, a $C_1$–$C_4$ alkylsulfonyl, a $C_1$–$C_4$ haloalkylsulfenyl, a $C_1$–$C_4$ haloalkylsulfinyl, a $C_1$–$C_4$ haloalkylsulfonyl, $NO_2$, CN, a phenyl and a phenoxy, Y, $Y_1$ and $y_2$ are each independently of each other H, a halogen, $C_1$–$C_4$ alkyl, a $C_1$–$C_4$ haloalkyl, a $C_1$–$C_4$ alkoxy, a $C_1$–$C_4$ haloalkyoxy, a $C_1$–$C_4$ alkylsulfenyl, $C_1$–$C_4$ alkylsulfinyl, a $C_1$–$C_4$ alkylsulfonyl, a $C_1$–$C_4$ haloalkylsulfenyl, a $C_1$–$C_4$ haloalkylsulfinyl, a $C_1$–$C_4$ haloalkylsulfonyl, $NO_2$ or CN, $Y_3$ is a $C_1$–$C_4$ alkyl or a $C_1$–$C_4$ haloalkyl, Ra is a $C_1$–$C_6$ alkyl, Rb is H, a $C_1$–$C_6$ alkyl, or a phenyl optionally substituted by $T^1$, Rc is a phenyl optionally substituted by on or more substituents as freely selected from a halogen, a $C_1$–$C_4$ alkyl, a $C_1$–$C_4$ alkoxy and a $C_1$–$C_4$ haloalkyl Rd is a benzoyl optionally substituted by on or more substituents as freely selected from a halogen, a $C_1$–$C_4$ alkyl, and a $C_1$–$C_4$ haloalkyl, Re is a $C_1$–$C_4$ alkyl, a $C_1$–$C_4$ haloalkyl, or a phenyl optionally substituted by $T^1$, Rf is $C_1$–$C_6$ alkyl, a $C_2$–$C_6$ alkenyl, a $C_1$–$C_6$ halogalkyl, a $C_2$–$C_4$ alkxyalkyl, a $C_3$–$C_6$ halocycloalkyl, a $C_1$–$C_4$ alkyl substituted by Rc, a $C_3$–$C_7$ cycloalkyl optionally substituted by a $C_1$–$C_4$ alkyl, a cycloalkyl substituted by Rc, a cyclopropyl nsubstituted by Rc and a $C_1$–$C_4$ alkyl, a $C_3$–$C_4$ cycloalkyl substituted by Rc and a halogen, a cyclopropyl substituted by $T^2$ and a $C_1$–$C_4$ alkyl, a $C_2$–$C_4$ alkenl subsituted by Rc, a $C_1$–$C_6$ alkoxy, a $C_1$–$C_4$ haloalkoxy, a $C_2$–$C_5$ alkenyloxy, a $C_3$–$C_6$ cycloalkoxy optionally substituted by a $C_1$–$C_3$ alkyl, a benzyloxy, COORa, —$NU^1NU^2$, a phenyl optionally substituted by $T^3$, a naphthyl, a pyridly optionally substituted by $T^1$, a phenyl $C_1$–$C_6$ alkyl or A-3, Rg and Rh are each indepenently of the other OH, a phenyl a $C_1$–$C_6$ alkyl, a $C_1$–$C_6$ alkoxy or a $C_1$–$C_4$ alkylsulfenyl, Ri, Rj and Rk are each indepentently of the other H, a $C_1$–$C_6$ alkyl, a $C_1$–$C_4$ alkenyl, a $C_3$–$C_6$ cycloalkyl optionally substituted by a $C_1$–$C_3$ alkyl or a benzyl, or any two of Ri, Rj and Rk may, together with the nitrogen atom to which ther are bonded, for a 5- or 8-membered ring group optionally containg an oxygen atom, a ntitogen atom or a sulfer atom, J is a pyrazolyl, an imidazolyl or a morpholinyl, $T^1$ is a halogen, a $C_1$–$C_4$ alkyl, a $C_1$–$C_4$ haloalkyl or a $C_1$–$C_4$ alkoxy, $T^2$ is a $C_2$–$C_4$ alkenyl optionally substituted by a halogen, $T^3$ is one of five substituents as freely selected from a halogen, $C_1$–$C_4$ alkyl, a $C_1$–$C_4$ haloalkyl, a $C_1$–$C_4$ alkoxy, $C_1$–$C_4$ alkylsulfenyl, a $C_1$–$C_4$ alkylsulfinyl, a $C_1$–$C_4$ alkylsulfonyl, a $C_1$–$C_4$ haloalkylsulfenyl, a $C_1$–$C_4$ haloalkylsulfinyl, a $C_1$–$C_4$ haloalkylsulfonyl, $NO_2$, CN, CHO, —$NU^1U^2$, a phenyl and a phennoxy, $U^1$ and $U^2$ are each independently of the other H, a $C_1$–$C_6$ alkyl, COORa, a phenyl or a benyzl, or $U^1$ and $U^2$ may, together with the nitrogen atom to which thay are bonded, from a 5- to 8-membered ring group optionally containg an oxygen atom, a nitrogen atom or a sulfer atom, m represents the number of substituents, and is 0, 1, 2 or 3, n represents the number of substituents, and is 0, 1, 2, 3 or 4, p represents the number of substituents, and is 0, 1 or 2, q represents the number of substituents, and is 0 or 1, (provided that when m, n or p is 2 or more, then the substituents may be the same or different).

2. Acrylonitrile compounds according to claim 1, wherein R is

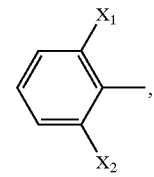

1-naphtyl, tertiary butyl or 2-pyridyl, $X_1$ is H, a halogen, a $C^1$–$C_4$ alkyl, a $C^1$–$C_4$ alkoxy, a $C^1$–$C_4$ haloalkyl or a phenyl, $X_2$ is H or a halogen, $R^1$ is H, a $C_1$–$C_6$ alkyl, a $C_3$–$C_7$ cycloalkyl, CN, COORa, CO(N-piperidyl), a $C_2$–$C_6$ alkylsulfenylalkyl, a $C_2$–$C_6$ alkoxyalkyl, $CH_3OC_2H_4OCH_2$, CONRaRb, a phenyl or $CH_2J$, A is A-3,
B is H, a $C^1$–$C_4$ alkyl, C(O)Rf, $SO_2$Re or a $C_2$–$C_4$ alkoxyalkyl,
Ra and Rb are each independently of the other a $C_1$–$C_6$ alkyl,
Rf is a $C_1$–$C_6$ alkyl, a $C_1$–$C_6$ alkoxy, a phenyl optionally substituted by a halogen, 2-pyridyl, 3-pyridyl, a phenyl $C_1$–$C_6$ alkyl or 5-pyrazolyl substituted by a $C_1$–$C_4$ alkyl,
Re is a $C_1$–$C_4$ alkyl or a phenyl,
$Y_1$ and $Y_2$ are each independently of the other H, a halogen, a $C_1$–$C_4$ alkyl, a $C^1$–$C_4$ haloalkyl or CN,
$Y_3$ is a $C^1$–$C_4$ alkyl, and
J is an N-pyrazolyl or N-morpholinyl.

3. Acrylonitrile compounds according to claim 2, wherein,
R is

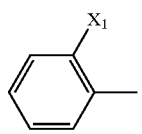

$X_1$ is H, a halogen or a $C_1$–$C_4$ alkyl,
$R^1$ is H, a $C_1$–$C_6$ alkyl or a $C_3$–$C_7$ cycloalkyl,
A is A-3,
B is H or C(O)Rf,
Rf is a $C_1$–$C_6$ alkyl, a phenyl or a phenyl $C_1$–$C_6$ alkyl,
$Y_1$ is a $C_1$–$C_4$ alkyl or a $C_1$–$C_4$ haloalkyl, and
$Y_2$ is a $C_1$–$C_4$ alkyl.

4. Acrylonitrile compounds according to claim 3, wherein
$X_1$ is H, a chlorine atom or methyl,
$R^1$ is H, methyl, ethyl, isopropyl, normal butyl or cyclohexyl,
B is H or C(O)Rf,
Rf is tertiary butyl, a phenyl or a benzyl,
$Y_1$ is methyl or trifluoromethyl, and
$Y_2$ is methyl.

5. Acrylonitrile compounds according to claim 3, wherein
$X_1$ is H,
$R^1$ is a $C_1$–$C_6$ alkyl,
B is C(O)Rf,
Rf is a $C_1$–$C_6$ alkyl,
$Y_1$ is a $C_1$–$C_4$ alkyl, and
$Y_2$ is a $C^1$–$C_4$ alkyl.

6. Acrylonitrile compounds according to claim 5, wherein
$X_1$ is H,
$R^1$ is methyl, ethyl, isopropyl or normal butyl,
B is C(O)Rf,
Rf is tertiary butyl,
$Y_1$ is methyl, and
$Y_2$ is methyl.

7. An agricultural chemical characterized by comprising, as an active ingredient, one or more acrylonitrile compounds according to claim 1.

8. An agricultural chemical characterized by comprising, as an active ingredient, one or more acrylonitrile compounds according to claim 2.

9. An agricultural chemical characterized by comprising, as an active ingredient, one or more acrylonitrile compounds according to claim 3.

10. An agricultural chemical characterized by comprising, as an active ingredient, one or more acrylonitrile compounds according to claim 4.

11. An agricultural chemical characterized by comprising, as an active ingredient, one or more acrylonitrile compounds according to claim 5.

12. An agricultural chemical characterized by comprising, as an active ingredient, one or more-acrylonitrile compounds according to claim 6.

* * * * *

UNITED STATES PATENT AND TRADEMARK OFFICE
CERTIFICATE OF CORRECTION

PATENT NO. : 6,642,234 B1
DATED : November 4, 2003
INVENTOR(S) : Ogura et al.

It is certified that error appears in the above-identified patent and that said Letters Patent is hereby corrected as shown below:

Column 61 to column 62,
Claim 1 should read:

-- 1. Acrylonitrile compounds of formula (1):

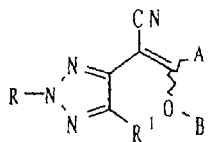

wherein,

R is a $C_1$-$C_6$ alkyl, a $C_3$-$C_7$ cycloalkyl optionally substituted by a $C_1$-$C_4$ alkyl, a phenyl optionally substituted by X, a naphthyl or a pyridyl, $R^1$ is H, a halogen, a $C_1$-$C_6$ alkyl, a $C_3$-$C_7$ cycloalkyl optionally substituted by a $C_1$-$C_4$ alkyl, a $C_1$-$C_6$ alkoxy, a $C_1$-$C_4$ haloalkyl, a $C_2$-$C_6$ alkoxyalkyl, $CH_3OC_2H_4OCH_2$, a $C_2$-$C_6$ alkylsulfenylalkyl, a $C_2$-$C_6$ alkylsulfinylalkyl, a $C_2$-$C_6$ alkylsulfonylalkyl, a $C_1$-$C_3$ alkyl substituted by phenyl, a phenyl, $C_7$-$C_{10}$ phenoxyalkyl, COORa, CONHRb, CONRaRb, CORa, CO(piperidyl), CN, $NO_2$ or $CH_2J$, A is

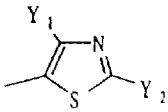

A-3

B is H, a $C_1$-$C_4$ alkyl, a $C_2$-$C_4$ alkoxyalkyl, $CH_2SCH_3$, $CH_2OC_2H_4OCH_3$, a $C_1$-$C_4$ alkyl substituted by Rc or Rd, a tetrahydropyranyl, $Si(CH_3)_3$, $SO_2Re$, $SO_2NHRb$, $SO_2NRaRb$, C(S)NHRb, C(S)NRaRb, $CH_2COORa$, C(O)Rf, P(O)RgRh, P(S)RgRh, an alkali metal, an alkaline earth metal or NHRiRjRk, X is one to three substituents as freely selected from a halogen, a $C_1$-$C_4$ alkyl, a $C_1$-$C_4$ haloalkyl, a $C_1$-$C_4$ alkoxy, a $C_1$-$C_4$ haloalkoxy, a $C_1$-$C_4$ alkylsulfenyl, a $C_1$-$C_4$ alkylsulfinyl, a $C_1$-$C_4$

UNITED STATES PATENT AND TRADEMARK OFFICE
CERTIFICATE OF CORRECTION

PATENT NO. : 6,642,234 B1
DATED : November 4, 2003
INVENTOR(S) : Ogura et al.

It is certified that error appears in the above-identified patent and that said Letters Patent is hereby corrected as shown below:

Column 61 to column 62 cont'd., alkylsulfonyl, a $C_1$-$C_4$ haloalkylsulfenyl, a $C_1$-$C_4$ haloalkylsulfinyl, a $C_1$-$C_4$ halo kylsulfonyl, $NO_2$, CN, a phenyl and a phenoxy, Y, $Y_1$ and $Y_2$ are each independently of the other H, a halogen, a $C_1$-$C_4$ alkyl, a $C_1$-$C_4$ haloalkyl, a $C_1$-$C_4$ alkoxy, a $C_1$-$C_4$ haloalkoxy, a $C_1$-$C_4$ alkylsulfenyl, a $C_1$-$C_4$ alkylsulfinyl, a $C_1$-$C_4$ alkylsulfonyl, a $C_1$-$C_4$ haloalkylsulfenyl, a $C_1$-$C_4$ haloalkylsulfinyl, a $C_1$-$C_4$ haloalkylsulfonyl, $NO_2$ or CN, $Y_3$ is a $C_1$-$C_4$ alkyl or a $C_1$-$C_4$ haloalkyl, Ra is a $C_1$-$C_6$ alkyl, Rb is H, a $C_1$-$C_6$ alkyl, or a phenyl optionally substituted by $T^1$, Rc is a phenyl optionally substituted by one or more substituents as freely selected from a halogen, a $C_1$-$C_4$ alkyl, a $C_1$-$C_4$ alkoxy and a $C_1$-$C_4$ haloalkyl Rd is a benzoyl optionally substituted by one or more substituents as freely selected from a halogen, a $C_1$-$C_4$ alkyl and a $C_1$-$C_4$ haloalkyl, Re is a $C_1$-$C_4$ alkyl, a $C_1$-$C_4$ haloalkyl, or a phenyl optionally substituted by $T^1$, Rf is a $C_1$-$C_6$ alkyl, a $C_2$-$C_6$ alkenyl, a $C_1$-$C_6$ haloalkyl, a $C_2$-$C_4$ alkoxyalkyl, a $C_3$-$C_6$ halocycloalkyl, a $C_1$-$C_4$ alkyl substituted by Rc, a $C_3$-$C_7$ cycloalkyl optionally substituted by a $C_1$-$C_4$ alkyl, a cycloalkyl substituted by Rc, a cyclopropyl substituted by Rc and a $C_1$-$C_4$ alkyl, a $C_3$-$C_4$ cycloalkyl substituted by Rc and a halogen, a cyclopropyl substituted by $T^2$ and a $C_1$-$C_4$ alkyl, a $C_2$-$C_4$ alkenyl substituted by Rc, a $C_1$-$C_6$ alkoxy, a $C_1$-$C_4$ haloalkoxy, a $C_2$-$C_5$ alkenyloxy, a $C_3$-$C_6$ cycloalkoxy optionally substituted by a $C_1$-$C_3$ alkyl, a benzyloxy, COORa, -$NU^1U^2$, a phenyl optionally substituted by $T^3$, a naphthyl, a pyridyl optionally substituted by $T^1$, a phenyl $C_1$-$C_6$ alkyl or A-3, Rg and Rh are each independently of the other OH, a phenyl, a $C_1$-$C_6$ alkyl, a $C_1$-$C_6$ alkoxy or a $C_1$-$C_4$ alkylsulfenyl, Ri, Rj and Rk are each independently of the other H, a $C_1$-$C_6$ alkyl, a $C_1$-$C_4$ alkenyl, a $C_3$-$C_6$ cycloalkyl optionally substituted by a $C_1$-$C_3$ alkyl or a benzyl, or any two of Ri, Rj and Rk may, together with the nitrogen atom to which they are bonded, form a 5- to 8-membered ring group optionally containing an oxygen atom, a nitrogen atom or a sulfur atom, J is a pyrazolyl, an imidazolyl or a morpholinyl, $T^1$ is a halogen, a $C_1$-$C_4$ alkyl, a $C_1$-$C_4$ haloalkyl or a $C_1$-$C_4$ alkoxy, $T^2$ is a $C_2$-$C_4$ alkenyl optionally substituted by a halogen, $T^3$ is one to five substituents as freely selected from a halogen, a $C_1$-$C_4$ alkyl, a $C_1$-$C_4$ haloalkyl, a $C_1$-$C_4$ alkoxy, a $C_1$-$C_4$ haloalkoxy, a $C_1$-$C_4$ alkylsulfenyl, a $C_1$-$C_4$ alkylsulfinyl, a $C_1$-$C_4$ alkylsulfonyl, a $C_1$-$C_4$ haloalkylsulfenyl, a $C_1$-$C_4$ haloalkylsulfinyl, a $C_1$-$C_4$ haloalkylsulfonyl, $NO_2$, CN, CHO, -$NU^1U^2$, a phenyl and a phenoxy, $U^1$ and $U^2$ are each independently of the other H, a $C_1$-$C_6$ alkyl, COORa, a phenyl or a benzyl, or $U^1$ and $U^2$ may, together with the nitrogen atom to which they are bonded, form a 5- to 8-membered ring group optionally containing an oxygen atom, a nitrogen atom or a sulfur atom, m represents the number of substituents, and is 0, 1, 2 or 3,

UNITED STATES PATENT AND TRADEMARK OFFICE
CERTIFICATE OF CORRECTION

PATENT NO. : 6,642,234 B1
DATED : November 4, 2003
INVENTOR(S) : Ogura et al.

It is certified that error appears in the above-identified patent and that said Letters Patent is hereby corrected as shown below:

Column 61 to column 62 cont'd., n represents the number of substituents, and is 0, 1, 2, 3 or 4,
p represents the number of substituents, and is 0, 1 or 2,
q represents the number of substituents, and is 0 or 1, (provided that when m, n or p is 2 or more, then the substituents may be the same or different). --

Column 62 to column 63,
Claim 2 should read:

-- 2. Acrylonitrile compounds according to claim 1, wherein
R is

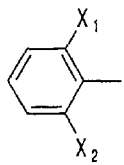

, 1-naphtyl, tertiary butyl or 2-pyridyl, $X_1$ is H, a halogen, a $C_1$-$C_4$ alkyl, a $C_1$-$C_4$ alkoxy, a $C_1$-$C_4$ haloalkyl or a phenyl,
$X_2$ is H or a halogen,
$R^1$ is H, a $C_1$-$C_6$ alkyl, a $C_3$-$C_7$ cycloalkyl, CN, COORa, CO(N-piperidyl), a $C_2$-$C_6$ alkylsulfenylalkyl, a $C_2$-$C_6$ alkoxyalkyl, $CH_3OC_2H_4OCH_2$, CONRaRb, a phenyl or $CH_2J$,
A is A-3,
B is H, a $C_1$-$C_4$ alkyl, C(O)Rf, $SO_2$Re or a $C_2$-$C_4$ alkoxyalkyl,
Ra and Rb are each independently of the other a $C_1$-$C_6$ alkyl,
Rf is a $C_1$-$C_6$ alkyl, a $C_1$-$C_6$ alkoxy, a phenyl optionally substituted by a halogen, 2-pyridyl, 3-pyridyl, a phenyl $C_1$-$C_6$ alkyl or 5-pyrazolyl substituted by a $C_1$-$C_4$ alkyl,
Re is a $C_1$-$C_4$ alkyl or a phenyl,
$Y_1$ and $Y_2$ are each independently of the other H, a halogen, a $C_1$-$C_4$ alkyl, a $C_1$-$C_4$ haloalkyl or CN,
$Y_3$ is a $C_1$-$C_4$ alkyl, and
J is an N-pyrazolyl or N-morpholinyl. --

UNITED STATES PATENT AND TRADEMARK OFFICE
CERTIFICATE OF CORRECTION

PATENT NO. : 6,642,234 B1
DATED : November 4, 2003
INVENTOR(S) : Ogura et al.

It is certified that error appears in the above-identified patent and that said Letters Patent is hereby corrected as shown below:

Column 64,
Lines 3-9, "$Y_2$ is a $C^1$-$C_4$ alkly." should read -- $Y_2$ is a $C_1$-$C_4$ alkyl. --.
Lines 33-35, "one or more-acrylonitrile compounds" should read -- one or more acrylonitrile compounds --.

Signed and Sealed this

Twenty-eighth Day of September, 2004

JON W. DUDAS
*Director of the United States Patent and Trademark Office*